United States Patent [19]

Kasha et al.

[11] Patent Number: 4,689,349

[45] Date of Patent: Aug. 25, 1987

[54] ANTI-TUMOR HALO BICYCLO ALKANONES

[75] Inventors: Walter J. Kasha, Los Angeles; Chantal S. Burnison, Beverly Hills, both of Calif.

[73] Assignee: CBD Corporation, Los Angeles, Calif.

[21] Appl. No.: 838,759

[22] Filed: Mar. 12, 1986

Related U.S. Application Data

[63] Continuation-in-part of Ser. No. 798,248, Nov. 8, 1985, abandoned, and Ser. No. 852,874, Nov. 7, 1984, abandoned, each is a continuation-in-part of Ser. No. 567,172, Dec. 30, 1983, abandoned, which is a continuation-in-part of Ser. No. 550,290, Nov. 8, 1983, abandoned, which is a continuation-in-part of Ser. No. 375,755, May 6, 1982, abandoned.

[51] Int. Cl.$^4$ .................... A61K 31/12; C07C 69/74
[52] U.S. Cl. .................................. 514/691; 514/530; 560/119; 568/374
[58] Field of Search ............... 514/530, 691; 560/119; 568/374

[56] References Cited

U.S. PATENT DOCUMENTS

| | | |
|---|---|---|
| 3,705,240 | 12/1972 | Bohner et al. .................. 424/203 |
| 4,000,174 | 12/1976 | Henrick et al. ................ 260/455 R |
| 4,292,432 | 9/1981 | Ono et al. ........................ 549/35 |
| 4,322,435 | 3/1982 | Kojima et al. .................. 424/305 |

FOREIGN PATENT DOCUMENTS

| | | |
|---|---|---|
| 65329 | 11/1975 | Australia . |
| 2193612 | 2/1974 | France . |
| 2419271 | 10/1979 | France . |
| 2040928 | 9/1980 | United Kingdom . |

OTHER PUBLICATIONS

Ford et al., "Anti-Neoplastic Effects of Metcyclor," 14th International Congress of Chemotherapy, Kyoto, Japan, Jun. 1985.

Ford et al., "Modulation of Connective Tissue Metabolism by Steroid Hormones and Ethocyn," 14th International Congress of Chemotherapy, Kyoto, Japan, Jun. 1985.

King et al., "Effects of Cyoctol vs. 13-Cis Retinoic Acid on Dihydrotestosterone Receptor Binding in Human Facial Sebacious Glands," 14th International Congress of Chemotherapy, Kyoto, Japan, Jun. 1985.

Ford et al., "Dense Intraabdominal Adhesions-A Manifestation of Localized Hyper-Androgen Receptors," 14th International Congress of Chemotherapy, Kyoto, Japan, Jun. 1985.

Ford et al., "Differential Androgen Receptor Activity in Patients with Androgenic alopecia and the Effects of Cyoctol on Dihydrotestosterone (DHT) Protein Binding" 14th International Congress of Chemotherapy, Kyoto, Japan, Jun. 1985.

King et al., "Effects of Cyoctol vs. 13-Cis Retinoic Acid on Dihydrotestosterone (DHT) Receptor Binding in Human Facial Skin Fibroblasts," 14th International Congress of Chemotherapy, Kyoto, Japan, Jun. 1985.

Hammill et al., "Effects of Cyoctol on the Hormonally Stimulated Increases in DNA and RNA Metabolism in Fungi" 14th International Congress of Chemotherapy, Kyoto, Japan, Jun. 1985.

Hammill et al., "Dihydrotestosterone and Estradiol Receptors in Trichomonas Vaginalis and the Effects of Cyoctol" 14th International Congress of Chemotherapy, Kyoto, Japan, Jun. 1985.

King et al., "Increased Androgen Binding in Keloids and its Inhibition with Cyoctol" 14th International Congress of Chemotherapy, Kyoto, Japan, Jun. 1985.

Selim et al., "Absorption, Tissue Distribution, Blood Level and Excretion of $^{14}C$ Labeled Cyoctol Following Oral or Dermal Administration", Abstract presented at 6th CIRD Symposium, Cannes, France, Oct. 1985.

Primary Examiner—Leonard Schenkman
Attorney, Agent, or Firm—Wegner & Bretschneider

[57] ABSTRACT

Potent tumor inhibitors are prepared which are compounds of the formula:

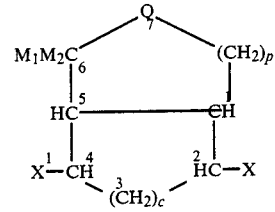

wherein
Q is CO, CH(OH) or C(OH)CH$_3$,
M$_1$ is halogen,
M$_2$ is halogen or hydrogen,
c is one or two
p is 0 or 1, and
one of X and X' is H and the other is hydroxy-C$^{2-9}$alkyl, methoxy-C$^{2-9}$-alkyl, ethoxy-C$^{2-9}$-alkyl, oxo-C$^{2-9}$-alkyl, formyl-C$^{2-9}$-alkyl, carboxy-C$^{2-9}$-alkyl or (C$_{1-2}$-alkyl)oxycarbonyl-C$^{2-9}$-alkyl.

21 Claims, No Drawings

ANTI-TUMOR HALO BICYCLO ALKANONES

This is a continuation-in-part of application Ser. No. 798,248, filed Nov. 8, 1985, (abandoned) and Ser. No. 852,874, filed Nov. 7, 1984 (abandoned) which are in turn a continuations-in-part of Ser. No. 567,172, filed Dec. 30, 1983, (abandoned) which in turn is a continuation-in-part of Ser. No. 550,290, filed Nov. 8, 1983, (abandoned) which in turn is a continuation-in-part of Ser. No. 375,755, filed May 6, 1982 (abandoned).

The present invention relates to a novel treatment of tumors, to halogenated bicyclo[3.2.0]heptane and bicyclo[3.3.0]octane derivatives and to compositions containing such derivatives useful for treatment of tumors. More specifically, this invention relates to the use in retarding and inhibiting development of tumors of a compound of the formula

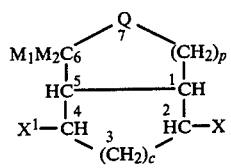

wherein
Q is CO, CH(OR) or CH(OCO-lower alkyl),
R is hydrogen or methyl,
$M_1$ is halogen,
$M_2$ is halogen or hydrogen,
p is zero or one and
c is one or two
one of X and X' is H and the other is hydroxyalkyl, methoxyalkyl, ethoxyalkyl, $C_{1-2}$-alkyloxycarbonyl-$C^{2-9}$alkyl, oxoalkyl, formylalkyl or carboxyalkyl in which the alkyl moiety of otherwise unspecified size contains 2–11 and preferably 2–9 carbon atoms;
and a pharmaceutically acceptable salt thereof.

As the pharmaceutically acceptable salts may be mentioned, for example, alkali metal salts, alkaline earth salts and ammonium salts. As specific salts may be mentioned sodium, magnesium and ammonium salts. As the lower alkyl group may be mentioned, for example, methyl, ethyl, straight chain or branched propyl and butyl. The alkyl moiety of 2 to 9 carbon atoms can represent ethyl, straight chain and branched propyl, butyl, pentyl, hexyl, heptyl, octyl and nonyl. Decyl and undecyl homologs are also useful.

The compounds of the invention in which p is zero are conveniently prepared by the following type of reaction sequence. Thus a suitably substituted cycloalkene of the formula

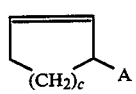

wherein A is X or X', but not hydrogen, is heated with a reagent capable of generating a dihaloketene of the formula $M_1M_2C=CO$. Typically used for generation can be a compound $M_1M_2CH-CO$-halogen, such as dichloroacetyl chloride, and a dehydrohalogenator, e.g. an amine such as triethylamine. The dihaloketene can also be generated from a trihaloacetyl halide by dehalogenation, e.g. using zinc activated with copper. This dihaloketene addition leads to formation of a mixture of isomers, in which the predominant one is the 2-A substituted 6-halogenated bicyclo[3.2.0]heptan-7-one of the formula

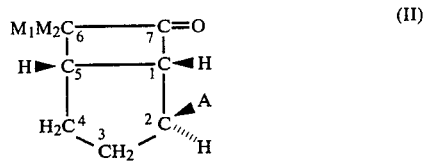

in the alpha form of that compound, as determined by nuclear magnetic resonance. In the predominant alpha configuration (alternatively designated as exo), the bridgehead protons and the A substituent are presumably situated on the same side of the ring plane. In the beta configuration (alternatively designated as endo), the bridgehead protons and the A substituent are presumably situated on opposite sides of the ring plane. Alpha compounds of type II are also preferred as anti-tumor agents. In this preferred group there are especially preferred compounds with a cis bridge that is with the bridgehead protons presumably situated on the same side of the ring plane. Also preferred are substituents in the 2-position of the formula $(CH_2)m-CH(O-E)G$, where E and G are H, methyl or ethyl; m is desirably four.

The second most frequent isomer in that mixture is the alpha form of the 2-A substituted 7-halogenated bicyclo[3.2.0]heptan-6-one of the formula

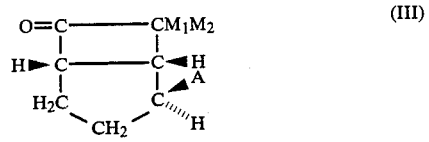

Also obtained, though in smaller amount, are the beta isomers, the A group being in a beta position.

Separation of these isomers can be accomplished by chromatographic separation. Conventional chromatography columns can be used employing silica or alumina to isolate the alpha 6,6-dihalo isomers. Thus silica gel is packed in a column using a standard slurry method. A solvent mixture of a non-polar and more polar solvent is used. The non-polar solvent is typically an alkane such as pentane, hexane, heptane or the corresponding cycloalkane. The more polar solvent can be an ether, an alkyl alkanoate such as ethyl acetate, an alkanol such as methanol or ethanol or a haloalkane such as dichloromethane or chloroform.

Isolation of the 7,7-dihalobicyclo[3.2.0]heptan-6-ones and 1,1-dihalohexahydro-2(1H)-pentalen-2-ones and their beta isomers has been carried out using high performance liquid chromatography.

The foregoing bicyclo[3.2.0]heptanes (p=0), can be converted to the bicyclo[3.3.0]octanes (p=1) by reaction with diazomethane.

Compounds of this invention and especially the 6-alpha isomers, have a high degree of biological activity, displaying especially excellent utility in their capacity to selectively inhibit development of malignant tumor cells, e.g. in adenocarcinoma, melanoma, embryonal and squamous tumors and teratoma. Special utility has been found in cancers known to be influenced by steroids. Inhibition has been specifically demonstrated in a wide variety of malignant tumor including those of breast, kidney and colon. A convenient bioassay for evaluation of this activity, in which these compounds show excellent results, is the Salmon clonogenic assay, *Cancer Res. Reports,* 65, p. 1, 1981, in which compounds at the level of 10 mcg/ml and lower (0.1 mcg/ml) cause selective destruction of tumor cells.

These compositions can be effectively administered topically in inert carriers suitable for that purpose, e.g. such alcohols as ethanol and 2-propanol, in salves, ointments, suspensions and emulsions.

It has also been observed that the compounds of this invention, on topical administration, increase elastin and decrease collagen, in that respect producing an effect resembling that of estrogens.

While topical application of compositions containing these compounds constitutes one embodiment of the invention, other routes for pharmaceutical administration are also contemplated, particularly the oral and suppository routes. Oral dosage unit formulations include tablets, capsules and other conventional oral forms. As a tablet the compounds are typically present in an amount of from about 1 to about 50% by weight, with the inert carrier constituting the remainder of the tablet. Tablets are compressed in a conventional manner, with typically one percent magnesium stearate being included in the mixture to be tabletted. Liquid oral dosage unit formulations may also be used in which the compounds are incorporated into vehicles conventionally used for lipid soluble compounds. Suppositories with the compounds are also contemplated, to provide a rectal suppository administration of the drug and which form takes advantage of the usual suppository ingredients. Capsules can employ the oily product, preferably diluted with an inert carrier.

The high potency of the 6-alpha compounds permits relatively low dosages both systemically via oral or suppository route or through topical (transdermal) application. A concentration of the compounds of from about 0.01 to 5 percent by weight of the composition is useful. Topical application on an infrequent basis, including a sustained release delivery, may indicate a relatively higher amount of the compounds, preferably in the range of from about 0.05 to about 3 percent by weight. A relatively lower concentration of the compounds is indicated where a relatively larger surface area is treated.

Where the compound is indicated for systemic delivery, oral, injection, suppository and sublingual forms may be used. Preferably the compound is administered as an oral dosage unit form, such as a tablet, capsule, powder or other traditional dosage unit form. In a preferred embodiment, the oral dosage unit form is a tablet which contains a relatively small amount of the compounds. A single oral dosage unit formulation, when administered as one oral dosage unit formulation several times per day, generally up to about four times per day, will for a adult male of average weight comprises an amount of about 0.01 to about 100 mg per oral dosage unit form, and preferably from about 10 mg to about 100 mg per oral dosage unit form.

The compounds of formula I are valuable chemical intermediates. Dehalogenation, i.e. conversion of both the $M^1$ and $M^2$ groups to hydrogen, e.g. with zinc, yields potent anti-androgens useful in treatment of acne, keloids and male pattern baldness.

The following examples illustrate the invention. For the sake of comprehensiveness, two methods of nomenclature have been used in providing the name for each compound. The Chemical Abstract naming system directly follows the applicants' naming system where they differ. The Chemical Abstract name is set off by brackets {}.

EXAMPLE 1A

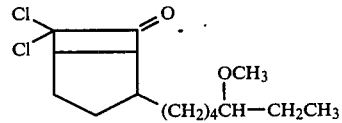

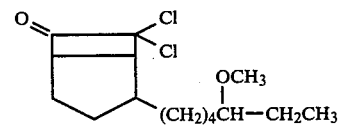

Alpha and beta isomers of 6,6-dichloro-2-(5-methoxyhept-1-yl)bicyclo[3.2.0]heptan-7-one {7,7-dichloro-4-(5-methoxyheptyl)bicyclo[3.2.0]heptan-6-one} and 7,7-dichloro-2-(5-methoxyhept-1-yl)bicyclo[3.2.0]heptan-6-one {7,7-dichloro-2-(5-methoxyheptyl)bicyclo[3.2.0]heptan-6-one}

Magnesium metal turnings (7.2 g, 0.299 moles) are added to a three-necked, round-bottomed flask equipped with a Friedrich condenser and kept under nitrogen gas. Tetrahydrofuran (300 ml) is transferred to the flask and the contents stirred. A clear, colorless solution of 1-chloro-5-methoxyheptane (48.1 g, 0.292 moles) is added portionwise and refluxed. The final third portion is added and the mixture stirred for 3 hours. The dark yellow solution is cooled to −25° C., the condenser is removed and replaced with a dry ice addition funnel. A clear solution of 3-chlorocyclopentene (29.9 g, 0.292 moles) is added over one hour. The solution is poured into a saturated ammonium chloride solution and stirred for one hour. The organic phase is separated and the aqueous phase is extracted with ether. The combined organic solutions are dried over anhydrous sodium sulfate. The solvent is removed under vacuum and the crude product is then purified by fractional distillation, yielding 3-(5-methoxyhept-1-yl)cyclopentene {3-(5-methoxyheptyl)cyclopentene} as a clear, colorless oil.

An alternative method of preparing the starting material is as follows: 3-(5-hydroxyhept-1-yl)cyclopentene {3-(5-hydroxyheptyl)cyclopentene} (10 g, 0.054 moles) is added to a solution containing potassium hydroxide (12.3 g, 0.219 moles) partially dissolved in dimethyl sulfoxide (108 ml). The reaction is stirred and methyl iodide (15.3 g, 0.108 moles) is rapidly added. The solution is heated in a 30° C. water bath for 12 hours, after which time the reaction is poured into water (200 ml) and partitioned with methylene chloride. The organic layer is removed and the aqueous phase extracted with methylene chloride (2×100 ml). The extracts are combined and dried over anhydrous sodium sulfate. The solvent was removed under vacuum leaving a clear, colorless oil (7.4 g, 0.038 moles), BP 65° C./0.1 mm.

Analysis: IR: 3047, 2927, 2850, 2818, 1459, 1359, 1154, 1093, and 716 cm$^{-1}$.

To a 1,000 ml three-necked, round-bottomed flask, equipped with a reflux condenser containing 3-(5- methoxyhept-1-yl)cyclopentene {3-(5-methoxyheptyl)-cyclopentene} (15.0 g, 0.076 moles) in 300 ml of hexane, freshly distilled dichloroacetyl chloride (35.1 g, 0.240 moles) is added and the solution is stirred by a mechanical stirrer and heated to reflux. Triethylamine (25.2 g, 0.249 moles), dissolved in 200 ml hexane, is added dropwise and the refluxing solution allowed to stir for 4 hours. The solvent is removed and then the residue is distilled and applied to a silica gel chromatography column of 4.5 cm diameter in a 4:1 hexane-ether solvent mixture. The product is eluted using a 4:1 hexane-ether solvent system. The fractions are monitored using vapor phase chromatography. The solvent is removed under vacuum. 6,6-Dichloro-2-(5-methoxyhept-1-yl)bicyclo[3.2.0]heptan-7-one {7,7-dichloro-4-(5-methoxyheptyl)bicyclo[3.2.0]heptan-6-one} and a smaller amount of 7,7-dichloro-(5-methoxyhept-2-yl)bicyclo[3.2.0]heptan-6-one {7,7-dichloro-2-(5-methoxyheptyl)bicyclo[3.2.0]heptan-6-one} were obtained in mainly the alpha form.

Infrared analysis shows maxima at 2963, 2932, 2864, 2857, 2820, 1803, 1461, 1378, 1223, 1197, 1157, 1093, 1030, 968, 914, 842, 821, 802, 778, 740, and 673 cm$^{-1}$. Substitution of C$^{14}$-labeled dichloroacetyl chloride yields the C$^{14}$-labeled isomers of the 6,6-dichloro and 7,7-dichloro derivatives above.

An alternative method of preparing the compound uses the following procedure, described in Example 26A substituting the starting material, 3-(5-methoxyhept-1-yl)cyclopentene {3-(5-methoxyheptyl)cyclopentene} (7.4 g, 0.038 moles), trichloroacetyl chloride (6.9 g, 0.038 moles), and phosphorous oxchloride (5.8 g, 0.038 moles). The crude product is kugelrohred and fractionally distilled under reduced pressure leaving a clear, colorless oil (8.1 g, 0.026 moles), BP 138° C./0.1 mm.

Analysis: IR: 2963, 2932, 2864, 2857, 2820, 1803, 1461, 1378, 1223, 1197, 1157, 1093, 1030, 968, 914, 842, 821, 802, 778, and 673 cm$^{-1}$.

EXAMPLE 1B

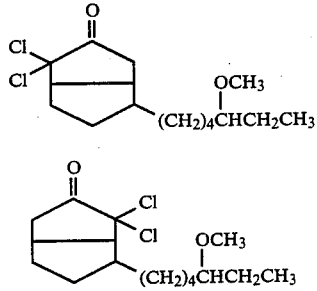

Alpha and beta isomers of
6,6-dichloro-2-(5-methoxyhept-1-yl)bicyclo[3.3.0]octan-7-one
{1,1-dichlorohexahydro-4-(5-methoxyheptyl)-2(1H)-pentalenone} and 8,8-dichloro-2-(5-methoxyhept-1-yl) bicyclo[3.3.0]octan-7-one
{1,1-dichlorohexahydro-6-(5-methoxyheptyl)-2(1H)-pentalenone}

A solution of 5 g of the isomers obtained in Example 1A in 100 ml of ether is transferred to a 500 ml round bottom flask. Excess diazomethane is generated from 60 g of N-methyl-N-nitroso-p-toluenesulfonamide by reacting with potassium hydroxide in methanol. The reaction is allowed to proceed for 50 minutes after which glacial acetic acid is added portionwise to destroy the excess diazomethane. The solution is extracted with ether and dried over anhydrous sodium sulfate. The solvent is removed under vacuum, leaving an orange oil. This oil is applied to a silica gel chromatography column; elution with a 4:1 mixture of hexane and ether and evaporation of the solvent yields the product as a clear liquid. Infrared maxima are observed at 2959, 2934, 2873, 2858, 2820, 1768, 1462, 1404, 1379, 1366, 1193, 1145, 1094, 923, 897, 778, 713, 663, 656, and 652 cm$^{-1}$. Substitution in this reaction of the individual isomers obtained by the separation procedure leads to the corresponding alpha and beta isomers of 6,6-dichloro-2-(5-methoxyhept-1-yl)bicyclo[3.3.0]octan-7-one {1,1-dichlorohexahydro-4-(5-methoxyheptyl)-2(1H)-pentalenone} and 8,8-dichloro-2-(5-methoxyhept-1-yl)bicyclo[3.3.0]octan-7-one {1,1-dichlorohexahydro-6-(5-methoxyheptyl)-2(1H)-pentalenone}.

EXAMPLE 2A

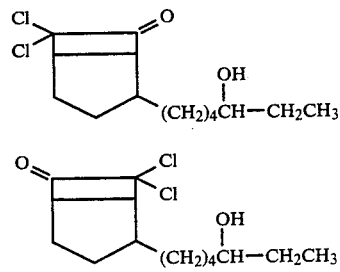

Alpha and beta isomers of
6,6-dichloro-2-(5-hydroxyhept-1-yl)bicyclo[3.2.0]heptan-7-one
{7,7-dichloro-4-(5-hydroxyheptyl)bicyclo[3.2.0]heptan-6-one} and
7,7-dichloro-2-(5-hydroxyhept-1-yl)bicyclo[3.2.0]heptan-6-one
{7,7-dichloro-2-(5-hydroxyheptyl)bicyclo[3.2.0]heptan-6-one}

To a solution of acetonitrile (140 ml) containing a mixture of the isomers of dichloro-2-(5-methoxyhept-1-yl)bicyclo[3.2.0]heptanones (30.6 g) obtained as in Example 1A is added sodium iodide (31.4 g) and trimethylsilyl chloride (11.4 g moles). The solution is stirred under an inert atmosphere for four hours after which time 50 ml water is added; the solution changes to a clear red color. The mixture is extracted with diethyl ether (150 ml) and the aqueous phase is discarded. The ether phase is washed with solutions of saturated sodium thiosulfate (75 ml) and brine (100 ml). The solvent is removed under vacuum leaving a clear, light yellow oil. The crude product contains a mixture of the starting material, the desired alcohols, and by-products. This mixture is applied on a chromatography column using a 4:1 hexane-ether mixture and eluted with 4:1 hexane-ether. Vacuum distillation at 0.1 mm pressure and about 130° C. yields a mixture of the alpha and beta isomers of 6,6-dichloro-2-(5-hydroxyhept-1-yl)bicyclo[3.2.0]heptan-7-one {7,7-dichloro-4-(5-hydroxyheptyl) bicyclo[3.2.0]heptan-6-one} and 7,7-dichloro-2-(5-hydroxyhept-1-yl)bicyclo[3.2.0]heptan-6-one {7,7-dichloro-2-(5-hydroxyheptyl) bicyclo[3.2.0]heptan-6-one}.

Infrared absorption maxima are observed at 3584, 3534, 3389, 3377, 2959, 2934, 2871, 2856, 1804, 1462, 1409, 1378, 1337, 1317, 1301, 1279, 1252, 1250, 1245, 1180, 1159, 1134, 1119, 1090, 1031, 965, 923, 896, 864, 811, 779, 742 and 676 cm$^{-1}$.

EXAMPLE 2B

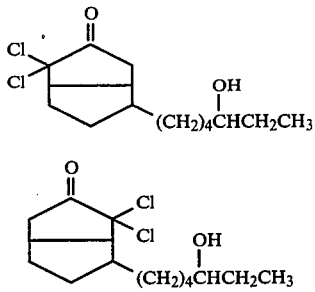

Alpha and beta isomers of 6,6-dichloro-2-(5-hydroxyhept-1-yl) bicyclo[3.3.0]octan-7-one {1,1-dichlorohexahydro-4-(5-hydroxyheptyl)-2(1H)-pentalenone} and 8,8-dichloro-2-(5-hydroxyhept-1-yl) bicyclo[3.3.0]octan-7-one {1,1-dichlorohexahydro-6-(5-hydroxyheptyl)-2(1H)-pentalenone}

Demethylation of alpha 6,6-dichloro-2-(5-methoxyhept-1-yl) bicyclo[3.3.0]octan-7-one {1,1-dichlorohexahydro-4-(5-methoxyheptyl)-2(1H)-pentalenone} by the procedure of Example 2A produces alpha 6,6-dichloro-2-(5-hydroxyhept-1-yl)bicyclo[3.3.0]-octan-7-one {1,1-dichlorohexahydro-4-(5-hydroxyheptyl)-2(1H)-pentalenone}. Infrared maxima occur at about 3416, 2955, 2868, 2856, 1801, 1462, 1131, 1118, 1029, 987, 967, 741 and 675 cm$^{-1}$.

Demethylation of 8,8-dichloro-2-(5-methoxyheptyl)bicyclo[3.3.0]octan-7-one {1,1-dichlorohexahydro-6-(5-methoxyheptyl)-2(1H)-pentalenone} gives 8,8-dichloro-2-(5-hydroxyhept-yl)bicyclo[3.3.0]octan-7-one {1,1-dichlorohexahydro-6-(5-hydroxyheptyl)-2(1H)-pentalenone}.

EXAMPLE 3

Separation of isomers

The product obtained by the dichloroketene reaction with 3-(5-methoxyhept-1-yl)cyclopentene {3-(5-methoxyheptyl)cyclopentene} in Example 1A yields a product containing 2 different regio isomers in addition to the beta and alpha forms. The reaction of this isomeric product with trimethylsilyl iodide according to Example 2A forms a demethoxylated product which also contains the same group of isomers. Both gas chromatography and high performance liquid chromatography confirm the presence of the three principal isomers in this group of 4 isomers. The fourth isomer appears to be present in a quantity less than 1%.

Identification and separation of the three principal isomers can be accomplished by use of a Beckman high performance liquid chromatograph equipped with a 165 variable wavelength detector. A Beckman 15 cm C-18 column with 5 micron packing was used for all analytical determinations. A 60%:40% acetonitrile:water solvent is used with a flow rate of 1 ml/min. The detector has wavelength scanning capabilities making it possible to determine the lambda maximum of these isomers. All three major peaks detected by the system had identical UV scans from 200-350 lambda with a lambda max 1 of 213 nm and a lambda max 2 of 319 nm, consistent with a carbonyl group in the chemical structure.

Separation of the isomers is accomplished using a Watman Magnum 20 column with 50 micron packing of C-18. A 0.5 g sample of the isomeric mixture is dissolved in 1.5 ml of acetonitrile. A 60%:40% acetonitrile:water solvent system is used with a flow rate of 20 ml/min. The detector monitors the samples at 210 and 318 nm. A total of 80 tubes (10 ml each) was collected and the samples were analyzed for the desired isomers by capillary gas chromatography. The appropriate tubes were then pooled together and the acetonitrile removed under vacuum. The aqueous phase was extracted with ether and the solvent again removed under vacuum and dried over anhydrous sodium sulfate, leaving clear yellow oils of 0.2 g of alpha 6,6-dichloro-2-(5-hydroxyhept-1-yl)bicyclo [3.2.0]heptan-7-one {7,7-dichloro-4-(5-hydroxyheptyl)bicyclo [3.2.0]heptan-6-one} and 0.1 g of alpha 7,7-dichloro-2-(5-hydroxyhept-1-yl)bicyclo[3.2.0]heptan-6-one {7,7-dichloro-2-(5-hydroxyheptyl)bicyclo[3.2.0]heptan-6-one}.

The alpha 6,6-dichloro-2-(5-hydroxyhept-1-yl)bicyclo[3.2.0]heptan-7-one {7,7-dichloro-4-(5-hydroxyheptyl)bicyclo[3.2.0]heptan-6-one} gives the following key NMR resonances: 1H 3.82, doublet (1H), 3.53 multiplet (1H), 3.37 (d of d) 1H, 2.40 quartet (1H), 0.944 triplet (3H). In the case of the alpha 7,7-dichloro compound, eluted thereafter, the following NMR regions were noted: 1H 4.03 d of d (1H), 3.53 multiplet (1H), 3.07 doublet (1H), 2.40 quartet (1H) and 0.948 triplet (3H). Besides the alpha 7,7-dichloro compounds, smaller quantities of beta isomers are eluted. The following NMR resonances are noted, 3.94 d of d (1H), 3.53 multiplet (1H), 3.42 d of d (1H), 0.94 triplet (3H).

The alpha 6,6-dichloro-2-(5-hydroxyhept-1-yl)bicyclo[3.2.0]heptan-7-one {7,7-dichloro-4-(5-hydroxyheptyl)bicyclo[3.2.0]heptan-6-one} can also be obtained from the mixture of alpha and beta 6,6-dichloro and 7,7-dichloro isomers by applying the crude mixture directly on a flash chromatography column (e.g. 2.5 cm diameter, 200-430 mesh) and eluting with a 6:1 hexane-ether (v/v) solution, collecting fractions in 20 ml tubes. The presence of the alpha 6,6-dichloro product in tubes can be determined by gas chromatography by comparison with the pure alpha 6,6-dichloro product obtained above using high performance liquid chromatography.

Structural assignment of alpha 6,6-dichloro-2-(5-hydroxyhept-1-yl)bicyclo[3.2.0]heptan-7-one {7,7-dichloro-4-(5-hydroxyheptyl)bicyclo[3.2.0]heptan-6-one}.

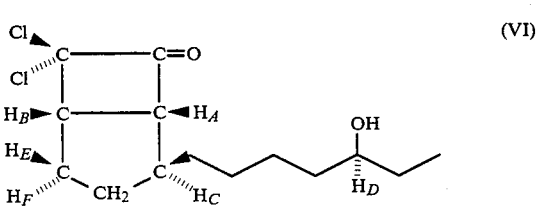

-continued

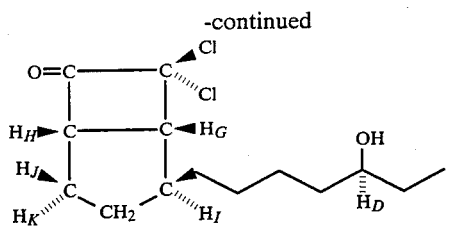
(V)

The resonance at 3.8 is due to the proton HA, coupled to the proton HB giving a doublet (8 Hz). Such a large coupling constant is due to the bridgehead protons, HA and HB, shown in the structure above. The resonance at 3.53 is ascribed to HD, the methine proton on the aliphatic chain. At 3.37, what appears to be a triplet is actually a doublet of doublets as it is due to HB, the other bridgehead proton. The proton HB is coupled to HA and largely one of the protons HE. Based on molecular models it is most likely that the bond angle of HB and HF (beta) is close to 90° and therefore the coupling constant is very small compared to HE (alpha). There is a clean quartet at 2.4, most likely due to proton HF. As a result of the cupped shape of the molecule from the fused rings the beta chlorine atom is in closer proximity to proton HF; therefore, there results a downfield shift. Irradiation of HA collapses the apparent triplet at 3.37 to a doublet, since the coupling of HB to HE is unaffected by the irradiation. Irradiation of HB collapses the doublet of HA to a singlet, which is also consistent with the proposed alpha 6,6-dichloro isomer structure. If this were actually the beta 6,6-dichloro isomer then proton HA should be coupled to HC and HA would appear as an apparent triplet.

Identification of alpha 7,7-dichloro-2-(5-hydroxyhept-1-ylbicyclo[3.2.0]heptan-6-one {7,7-dichloro-2-(5-hydroxyheptyl) bicyclo[3.2.0]heptan-6-one}

There is an apparent triplet at 4.03, which is actually a doublet of doublets due to the coupling of HH with the protons of HG and HJ and shifted further downfield as a result of being located on the carbon adjacent to the carbonyl. There may be a small coupling of proton HH with HK (less than 1 Hz). There is also a quartet at about 2.4 ppm due to proton HK. A doublet corresponding to proton HG at 3.07 is due to the coupling of proton HG to proton HH. There may be a small coupling with proton HI but based on molecular models the bond angles between these protons would be less than 1 Hz. Irradiation of proton HH collapses the doublet (due to proton HG) to a singlet which is also consistent with the 7,7-dichloro isomer structure. Irradiation of HG results in the change in the resonance of proton HH from an apparent triplet (actually doublet of doublets) to a doublet.

If the aliphatic chain were in the beta position instead of the alpha position, proton HG would be coupled to HI and thus give a resonance of an apparent triplet (doublet of doublets) instead of a doublet at 3.07. Based on molecular models the bond angle between proton HG and HI is almost 90° and would therefore have a very small coupling.

EXAMPLE 4A

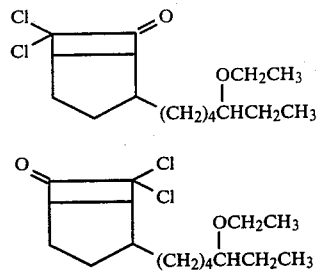

Alpha and beta isomers of 6,6-dichloro-2-(5-ethoxyhept-1-yl)bicyclo[3.2.0]heptan-7-one {7,7-dichloro-4-(5-ethoxyheptyl)bicyclo[3.2.0]heptan-6-one} and 7,7-dichloro-2-(5-ethoxyhept-1-yl)bicyclo[3.2.0]heptan-6-one {7,7-dichloro-2-(5-ethoxyheptyl)bicyclo[3.2.0]heptan-6-one}

Ethyl 5-ethoxyheptanoate

A mixture of 400 g 5-hydroxyheptanoic acid and 6-ethyltetrahydro-2H-pyran-2-one (400 g) is added to the reaction vessel containing ethanol (4000 ml) and triethylorthoformate (4000 ml). Perchloric acid (160 ml) is slowly added. The mixture is stirred at room temperature for 4 hours, after which time sodium hydroxide pellets (230 g) are added to stop the reaction. Once the sulfuric acid has been neutralized the ethanol and triethylorthoformate are removed under vacuum. The residue is partitioned between ether (2000 ml) and water (1000 ml). The organic phase is separated and the aqueous layer extracted with ether (3×500 ml). The organic layers are combined and dried over anhydrous sodium sulfate. The remaining solvent is removed under vacuum leaving a clear orange oil. The crude product is fractionally distilled under reduced pressure leaving a clear, colorless oil (302 g, 1.49 moles), BP 120° C./10 cm Hg.

Analysis: IR: 2971, 2933, 2874, 1736, 1461, 1448, 1418, 1400, 1372, 1348, 1300, 1241, 1196, 1177, 1106, 1076, 1035, 1014, 968, 921, 856, and 826 cm$^{-1}$.

5-Ethoxyheptanol

A solution of tetrahydrofuran (2000 ml) containing lithium aluminum hydride (46 g, 1.21 moles) is cooled in a −60° C. dry ice/ethanol bath. Ethyl 5-ethoxyheptanoate (302 g, 1.49 moles) is diluted in tetrahydrofuran (300 ml) and added dropwise to the stirring reaction. After the addition is complete the reaction is warmed to room temperature and stirred an additional hour. The solution is again cooled in a −78° C. dry ice/ethanol bath and the excess hydride is destroyed by adding dropwise the following: water (46 ml), 15% sodium hydroxide solution (46 ml), and water (136 ml). The reaction is filtered and the solids washed several times with tetrahydrofuran (3×500 ml). The volume of the filtrate is reduced under vacuum and the residue dried over anhydrous magnesium sulfate. The remaining solvent is then removed leaving a clear, colorless oil suitably pure for the next reaction (238 g, 1.49 moles).

Analysis: IR: 3397 (broad), 2971, 2937, 2872, 1460, 1448, 1403, 1380, 1372, 1346, 1107, 1076, and 975 cm$^{-1}$.

1-Chloro-5-ethoxyheptane

5-Ethoxyheptanol (238 g, 1.49 moles) is diluted in pyridine (128 g, 1.62 moles). The solution is stirred at room temperature and thionyl chloride (388 g, 3.22 moles) is added dropwise over 2 hours. After this time the mixture is heated in a 70° C. water bath for 2 additional hours. Water (700 ml) is added to the reaction and the organic layer separated. The aqueous layer is extracted with hexane (3×400 ml) and the extracts are combined with the organic phase. The organic phase then is washed with a 10% hydroxide solution (1000 ml). The solvent volume is reduced under vacuum and the residue is dried over anhydrous magnesium sulfate. The remaining solvent is removed leaving a clear light yellow oil. The crude product is fractionally distilled under reduced pressure leaving a clear, colorless oil (162 g, 1.13 moles), BP 96° C./9.5 cm Hg.

Analysis: IR: 2968, 2933, 1459, 1445, 1400, 1370, 1344, 1309, 1157, 1107, 1076, 994, 979, 734, and 649 cm$^{-1}$.

3-(5-Ethoxyhept-1-yl)cyclopentene {3-(5-Ethoxyheptyl)cyclopentene}

The procedure followed is the same as that described in Example 20 substituting 1-chloro-5-ethoxyheptane (162 g, 1.13 moles) diluted in tetrahydrofuran (162 ml), granular magnesium (50 g, 2.1 moles) in tetrahydrofuran (500 ml), Li$_2$CuCl$_4$ (29.1 m moles), and 3-chlorocyclopentene (89 g, 0.86 moles) diluted in tetrahydrofuran (100 ml).

The desired mixture of the alpha and beta isomers of of 6,6-dichloro-2-(5-ethoxyhept-1-yl)bicyclo[3.2.0]heptan-7-one {7,7-dichloro-4-(5-ethoxyheptyl)bicyclo[3.2.0]heptan-6-one} and 7,7-dichloro-2-(5-ethoxyhept-1-yl)bicyclo[3.2.0]heptan-6-one {7,7-dichloro-2-(5-ethoxyheptyl)bicyclo[3.2.0]heptan-6-one} is prepared by the procedure as that described in Example 26A, 3-(5-ethoxyhept-1-yl)cyclopentene {3-(5-ethoxyheptyl)cyclopentene} (170 g, 0.573 moles) dissolved in ether (1700 ml), trichloroacetyl chloride (187 g, 1.03 moles), phosphorous oxychloride (158 g, 1.03 moles) both dissolved in ether (500 ml), and zinc/copper couple (75 g, 1.15 moles) are used. The crude product is kuglerohred and subsequently fractionally distilled under reduced pressure leaving a clear, colorless oil (108 g, 0.338 moles), BP 145° C./0.31 mm.

Analysis: IR: 2965, 2931, 2862, 1803, 1480, 1461, 1450, 1400, 1370, 1345, 1225, 1107, 1080, 1028, 970, 822, 800, 738, 725, 670, and 654 cm$^{-1}$.

EXAMPLE 4B

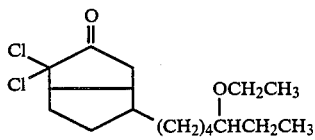

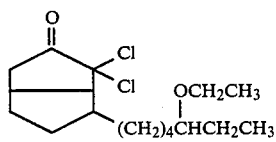

Alpha and beta isomers of 6,6-dichloro-2-(5-ethoxyhept-1-yl)bicyclo[3.3.0]octan-7-one {1,1-dichloro-4-(5-ethoxyheptyl)hexahydro-2(1H)-pentalenone} and 8,8-dichloro-2-(5-ethoxyhept-1-yl-bicyclo[3.3.0]octan-7-one {1,1-dichloro-6-(5-ethoxyheptyl)hexahydro-2(1H)-pentalenone}

Diazomethane is generated in situ from N-methyl-N-nitroso-p-toluenesulfonamide (60 g) using the macro diazald kit (Aldrich). The product of Example 4A, 6,6-dichloro-2-(5-ethoxyhept-1-yl) bicyclo[3.2.0]heptan-7-one {7,7-dichloro-4-(5-ethoxyheptyl)bicyclo[3.2.0]heptan-6-one} and isomers (36 g, 0.113 moles), is treated with an ethereal diazomethane solution (100 ml) followed by methanol (4 ml).

After 50 minutes the excess diazomethane is neutralized with the addition of acetic acid (10 ml). The solvent is removed under vacuum leaving a clear yellow liquid. The crude product is then diluted with acetic acid (240 ml) and stirred while zinc powder (72 g, 1.10 moles) is slowly added. The reaction is heated in a 70° C. water bath for 1 hour, after which time ether (500 ml) is added and the solution filtered. The filtrate is washed with brine (100 ml) and then with a solution of saturated bicarbonate. The ether layer is separated and dried over anhydrous sodium sulfate. The solvent is removed under vacuum leaving a clear yellow oil. The crude product is chromatographed on silica gel and subsequently kugelrohred under vacuum leaving a clear, colorless oil (12 g, 0.045 moles).

Analysis: IR: 2964, 2930, 2859, 1741, 1461, 1404, 1369, 1343, 1300, 1241, 1157, 1109, 1080, 875, and 797 cm$^{-1}$.

EXAMPLE 5A

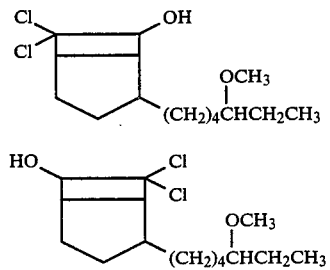

Alpha and beta isomers of 6,6-dichloro-2-(5-methoxyhept-1-yl)bicyclo[3.2.0]heptan-7-ol {7,7-dichloro-4-(5-methoxyheptyl)bicyclo[3.2.0]heptan-6-ol} and 7,7-dichloro-2-(5-methoxyhept-1-yl)bicyclo[3.2.0]heptan-6-ol {7,7-dichloro-2-(5-methoxyheptyl)bicyclo[3.2.0]heptan-6-ol}

Sodium borohydride (0.2 g) is added in one portion to 80 ml of ethanol. Alpha and beta isomers of 6,6-dichloro-2-(5-methoxyhept-1-yl)bicyclo[3.2.0]heptan-7-one {7,7-dichloro-4-(5-methoxyheptyl)bicyclo[3.2.0]heptan-6-one. (1 g) is added and the reaction mixture is heated at 45° C. for 10 hours. The solution is then cooled in an ice water bath and concentrated hydrochloric acid is added dropwise until the solution has reached a pH of 7. The reaction mixture is then extracted 3 times with 75 ml ether. The combined ether extracts are washed with sodium bicarbonate and dried over anhydrous sodium sulfate. The solvent is removed under vacuum, leaving 0.4 g of the alpha and beta isomers of 6, 6-dichloro-2-(5-methoxyheptl-yl)bicyclo[3.2.0]heptan-7-ol {7,7-dichloro-4-(5-methoxyheptyl)bicyclo[3.2.0]heptan-6-ol} and 7,7-dichloro-2-(5-methoxyhept-1-yl)bicyclo [3.2.0]heptan-6-ol {7,7-dichloro-2-(5-methoxyheptyl)bicyclo [3.2.0]heptan-6-ol} of a clear yellow product showing infared maxima at 3447 (broad), 2960, 2934, 2873, 2858, 2824, 1462, 1418, 1375, 1335, 1263, 1178, 1163, 1094, 1042, 962, 936, 920, 858, 849, 842 and 682 cm$^{-1}$.

EXAMPLE 5B

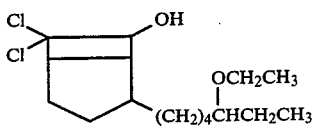

Substituting 1 g of 7,7-dichloro-2-(5-ethoxyhept-1-yl) bicyclo[3.2.0]heptan-6-one {7,7-dichloro-2-(5-ethoxyheptyl)bicyclo[3.2.0]heptan-6-one} using the procedure of the preceding example yields 7,7-dichloro-2-(5-methoxyhept-1-yl)bicyclo[3.2.0]heptan-6-ol {7,7-dichloro-2-(5-ethoxyheptyl)bicyclo[3.2.0]heptan-6-ol} with a very similar infrared spectrum.

EXAMPLE 5C

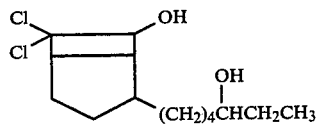

Substituting alpha 6,6-dichloro-2-(5-hydroxyhept-1-yl)bicyclo[3.2.0]heptan-7-one {7,7-dichloro-4-(5-hydroxyheptyl)bicyclo [3.2.0]heptan-6-one} of Example 2A as a starting material in Example 5A yields alpha 6,6-dichloro-2-(5-hydroxyhept-1-yl)bicyclo[3.2.0]heptan-7-ol {6,6-dichloro-alpha-ethyl-7-hydroxybicyclo[3.2.0]heptane-2-pentanol}.

EXAMPLE 6

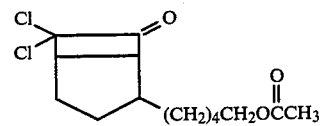

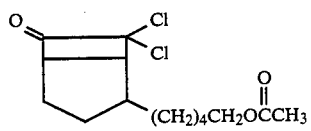

Alpha and beta isomers of
6,6-dichloro-2-(5-acetoxypent-1-yl) bicyclo[3.2.0]heptan-7-one
{4-[5-(acetyloxy)pentyl]-7,7-dichlorobicyclo[3.2.0]heptan-6-one} and
7,7-dichloro-2-(5-acetoxy-pent-1-yl)bicyclo[3.2.0]heptan-6-one
}2-[5-(acetyloxy)pentyl]-7,7-dichlorobicyclo[3.2.0]heptan-6-one}

The product of Example 22A, 6,6-dichloro-2-(5-hydroxypent-1-yl) bicyclo[3.2.0]heptan-7-one and isomers (518 g, 19 mmoles) is diluted with glacial acetic acid (10 ml) and stirred in a 70° C. water bath for 4 hours. The reaction is cooled to room temperature and partitioned between ether (50 ml). The ether layer is separated and the aqueous phase extracted with ether (2×50 ml). The organic extracts are combined and neutralized with a solution of saturated bicarbonate. The organic phase is dried over anhydrous sodium sulfate and the solvent removed under vacuum leaving a clear yellow oil. The crude product is chromatographed on silica gel and subsequently kugelrohred under vacuum leaving a clear, colorless oil (4.1 g, 0.013 moles).

EXAMPLE 7

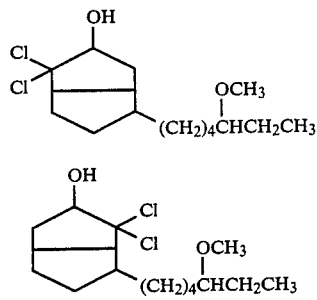

Alpha and beta isomers of
6,6-dichloro-2-(5-methoxyhept-1-yl) bicyclo[3.3.0]octan-7-ol
{1,1-dichlorooctahydro-4-(5-methoxyheptyl)-2-pentalenol} and
8,8-dichloro-2-(5-methoxyhept-1-yl)bicyclo [3.3.0]octan-7-ol
{1,1-dichlorooctahydro-6-(5-methoxyheptyl)-2-pentalenol}

The mixture of isomers obtained in Example 1B is subjected to the procedure of Example 5A yielding an orange oil. This oil is applied in hexane and ether to a silica gel chromatography column and elution with 4:1 hexane-ether yields the product as a clear liquid. Infrared maxima are observed at 3430, 2931, 2856, 1658, 1461, 1379, 1362, 1328, 1325, 1316, 1244, 1195, 1173, 1162, 1093, 1027, 984, 950, and 923 cm$^{-1}$. Substitution in this reaction of the individual isomers obtained in Example 2B leads to the corresponding alpha and beta isomers of 6,6-dichloro-2-(5-hydroxyhept-1-yl)bicyclo[3.3.0]octan-7-ol {4,4-dichloro-alphaethyloctahydro-5-hydroxy-1-pentalenepentanol} and 8,8-dichloro-2-(5-hydroxyhept-1-yl)bicyclo[3.3.0]octan-7-ol {6,6-dichloroalpha-ethyloctahydro-5-hydroxy-1-pentalenepentanol}, the alpha 6,6-dichloro isomer being the principal product.

EXAMPLE 8

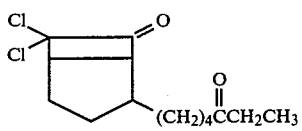

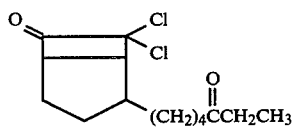

Alpha and beta isomers of
6,6-dichloro-2-(5-oxohept-1-yl)bicyclo
[3.2.0]heptan-7-one
{7,7-dichloro-4-(5-oxoheptyl)bicyclo
[3.2.0]heptan-6-one} and
7,7-dichloro-2-(5-oxohept-1-yl)bicyclo[3.2.0]heptan-6-one
{7,7-dichloro-2-(5-oxoheptyl)bicyclo[3.2.0]heptan-6-one}

A dry 100 ml 3-necked flask is heated and allowed to cool under nitrogen after which there is first added 2.3 g of the mixture of isomers obtained in Example 2A followed by 17 ml of dichloromethane. To the stirred reaction mixture there is added 6.4 g of pyridinium dichromate in a single portion. After 3 hours ether (4×50 ml) is added and the solution is shaken vigorously to dissolve any product trapped in the precipitated chromium salts. The solution is filtered through a sintered glass filter with a silica pad. The filtrate is washed successively with 75 ml of water and then 75 ml brine and dried over anhydrous sodium sulfate. The solvent is removed under vacuum leaving a clear yellow oil. The 5-oxohept-1-yl product is purified by silica gel chromatography using 4:1 hexane:ether (v/v) as the eluting solvent. The fractions containing the product, as determined by vapor phase chromatography, are pooled and the solvent is removed under vacuum leaving a clear yellow oil.

Separation of isomers yielding mainly the 6-alpha isomer follows the procedure of Example 3. Infrared maximum were observed at: 2932, 2859, 1799, 1707, 1653, 1457, 1410, 1371,1289, 1261, 1222, 1161, 1111, 1051, 1027, 963, 953, 915, 862, 843, 803, 733, and 671 cm$^{-1}$.

EXAMPLE 9

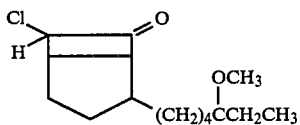

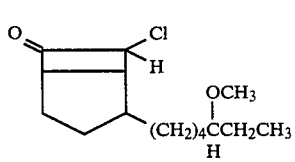

Alpha and beta isomers of
6-chloro-2-(5-methoxyhept-1-yl)bicyclo
[3.2.0]heptan-7-one
{7-chloro-4-(5-methoxyheptyl)bicyclo[3.2.0]heptan-6-one} and
7-chloro-2-(5-methoxyhept-1-yl)bicyclo[3.2.0]heptan-6-one
{7-chloro-2-(5-methoxyheptyl)bicyclo[3.2.0]heptan-6-one}

To a dry 100 ml 3-necked round bottom flask under nitrogen, equipped with a pressure equalizing dropping funnel, thermometer, and a magnetic stirrer, there is added the mixture of isomers obtained in Example 1A (5 g) and a catalytic amount (5 mg) of 2,2'-azobisisobutyronitrile. To the stirring solution there is added dropwise tri-n-butyltin hydride (4.7 g). The reaction mixture is maintained below 40° C. in a water bath. After the addition is complete the reaction mixture is stirred at 30° C. until a test of aliquot indicates the disappearance of the hydride, typically after about 3 hours. Then 35 ml water and 75 ml ether are added and the organic phase is separated and washed with 50 ml brine and dried over anhydrous sodium sulfate. Evaporation of the solvent under vacuum leaves the crude product, which is then chromatographed on silica gel using 4:1 hexane:ether (v/v) as the elution solvent. The fractions are pooled (as determined by VPC) and the solvent is removed under vacuum leaving the product as a clear colorless oil (2.5 g). Infrared maxima observed: 2960, 2932, 2871, 2855, 1804, 1461, 1448, 1034, 1023, 968, 817, 743, 703 and 676 cm$^{-1}$. Individual isomers are obtained by the method of Example 3.

EXAMPLE 10

3-(Hept-1-yl)cyclopentene {3-heptylcyclopentene}

The procedure followed is the same as that described in Example 20 substituting 1-bromoheptane (100 g, 0.56 moles) diluted in tetrahydrofuran (100 ml), granular magnesium (25 g) in tetrahydrofuran (100 ml), 0.1 M solution of Li$_2$CuCl$_4$ (1.7 mmoles), and 3-chlorocyclopentene (57 g, 0.56 moles) diluted in tetrahydrofuran (200 ml). The crude product is fractionally distilled under vacuum leaving a clear, colorless oil (49 g, 0.29 moles), BP 41° C./0.35 mm.

Analysis: IR: 3047, 2847, 2939, 2922, 2915, 2900, 2849, 1461, 1375, 1357, 1300, 1203, 1101, 1058, 975, 932, 910, 760, and 715 cm$^{-1}$.

EXAMPLE 11

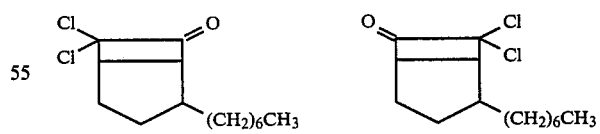

Alpha and beta isomers of
6,6-dichloro-2-(hept-1-yl)bicyclo [3.2.0]heptan-7-one
{7,7-dichloro-4-heptylbicyclo[3.2.0]heptan-6-one} and
7,7-dichloro-2-(hept-1-yl)bicyclo[3.2.0]heptan-6-one
{7,7- dichloro-2-heptylbicyclo[3.2.0]heptan-6-one}

The procedure followed is the same as that described in Example 21A substituting 3-(hept-1-yl)cyclopentene {3-heptylcyclopentene} (49 g, 0.30 moles) diluted in ether (490 ml), trichloroacetyl chloride (97 g, 0.53 moles) and phosphorous oxychloride (81 g, 0.53 moles) both diluted with ether (150 ml), and zinc/copper couple (30 g, 0.59 moles). The crude product is kugelrohred and subsequently fractionally distilled under reduced pressure leaving a clear, colorless oil (20.6 g, 0.075 moles), BP 115° C./0.22 mm.

Analysis: IR: 2955, 2925, 2853, 1803, 1464, 1451, 1380, 1225, 1030, 965, 815, 790, 740, 725, and 670 cm$^{-1}$.

EXAMPLE 12

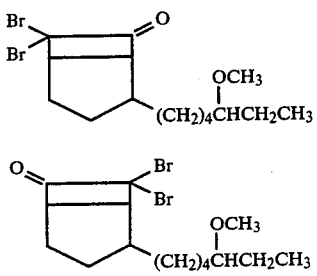

Alpha and beta isomers of
6,6-dibromo-2-(5-methoxyhept-1-yl)bicyclo
[3.2.0]heptan-7-one
{7,7-dibromo-4-(5-methoxyheptyl)bicyclo
[3.2.0]heptan-6-one} and
7,7-dibromo-2-(5-methoxy-1-yl)bicyclo
[3.2.0]heptan-6-one
{7,7-dibromo-2-(5-methoxyheptyl)bicyclo
[3.2.0]heptan-6-one}

Tribromoacetic acid (34.3 g) is added to a dry 500 ml 3-necked round bottom flask equipped with pressure equalizing dropping funnel, stirrer and condenser under nitrogen. Phosphorus tribromide (41.5 g) is added dropwise with stirring. The reaction is completed within 2 hours and the crude tribromoacetyl is distilled at about 75° C. and 10 mm.

Zinc-copper couple (6.5 g) and 15 g of 3-(5-methoxyhept-1-yl) cyclopentene {3-(5-methoxyheptyl)cyclopentene} dissolved in 100 ml of ether are added to a 500 ml 3-necked round bottomed flask equipped with a magnetic stirrer, reflux condenser, and a pressure equalizing dropping funnel. A solution of 15.1 g of tribromoacetyl bromide and phosphorus oxychloride (15.6 g) in 100 ml ether is added dropwise to the stirring solution for a period of over an hour to generate dibromoketene. The reaction mixture is heated to reflux and allowed to stir until no more starting material is present as evidenced by vapor phase chromatography. The excess dibromoketene and phosphorus oxychloride are destroyed by the dropwise addition of water. The crude product is filtered and the filtrate is washed with 100 ml brine and a saturated solution of 100 ml sodium bicarbonate until the pH reaches 7. The organic phase is washed again with 100 ml brine and dried over anhydrous sodium sulfate. The solvent is removed under vacuum leaving a brown liquid. The material is kugelrohred under vacuum and subsequently chromatographed on silica gel with 4:1 hexane:ether (v/v) as the elution solvent. The fraction is pooled (as determined by vapor phase chromatography) and the solvent removed under vacuum leaving a clear oil.

EXAMPLE 13

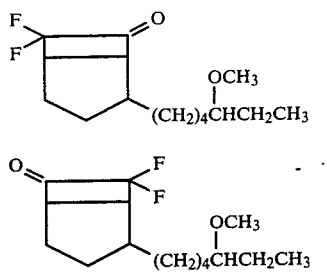

Alpha and beta isomers of
6,6-difluoro-2-(5-methoxy-hept-1-yl)
bicyclo[3.2.0]heptan-7-one
{7,7-difluoro-4-(5-methoxyheptyl)bicyclo[3.2.0]heptan-
6-one} and
7,7-difluoro-2-(5-methoxyhept-1-yl)bicyclo[3.2.0]heptan-6-one {7,7-difluoro-2-(5-methoxyheptyl)
bicyclo[3.2.0]heptan-6-one}

Chlorodifluoroacetic acid (50 g) is added to a 250 ml 3-necked flask. The flask is cooled in an ice water bath and stirred while 116.7 g of phosphorus tribromide are slowly added in the course of 5 minutes. After subsequent refluxing for 2 hours, the chlorodifluoroacetyl chloride is distilled into an ice-cooled receiver as a colorless liquid.

Zinc-copper couple (9.7 g) and 80 ml anhydrous acid is added to a dry 250 ml 3-necked round-bottom flask under a nitrogen atmosphere. Chlorodifluoroacetyl chloride (15.1 g) in 20 ml ether are added dropwise to the stirring solution and the etheral difluoroketene monomer is distilled into a receiver cooled in an ice water bath. 3-(5-Methoxyhept-1-yl)cyclopentene {3-(5-methoxyheptyl)cyclopentene} (15 g) is added to the distillate in 20 ml ether. The reaction is stirred for an hour after which time 50 ml of cold water are added. The solution is washed with 75 ml saturated sodium bicarbonate. The organic phase is separated, washed with 75 ml brine and dried over anhydrous sodium sulfate. The solvent is removed under vacuum leaving a green oil. The product is kugelrohred under reduced pressure and chromatographed on silica gel using a 4:1 hexane:ether (v/v) solvent system. The fractions are pooled (as determined by VPC) and the solvent removed under vacuum leaving a clear light yellow oil. Infrared maxima observed at: 2921, 2847, 2689, 2669, 2650, 2645, 2636, 2621, 2609, 2528, 2517, 2510, 2506, 1771, 1457, 1373, 1358, 1280, 1193, 1160, 1126, 1092, 968, 911, 838, 775, 715, 650 and 646 cm$^{-1}$.

EXAMPLE 14 5-Chloropentan-3-ol

5-Chloropentan-3-one {1-chloro-3-pentanone} (100 g, 0.83 moles) diluted in ethanol (100 ml) is added dropwise to a solution of sodium borohydride (8.6 g, 0.23 moles) dissolved in 95% ethanol (200 ml). The reaction is then stirred for an additional hour then cooled in an ice water bath. The excess hydride is neutralized by the slow addition of 15% sulfuric acid. The reaction is then partitioned between diethyl ether and water (150 ml and 300 ml, respectively). The organic phase is separated and the solvent removed under vacuum. The aqueous layer is extracted with ether (2×200 ml) and the ether extracts combined with the organic residue and washed with brine (300 ml). The ether phase is dried over anhydrous sodium sulfate and the remaining solvent is removed under vacuum leaving clear, yellow oil. The crude product is chromatographed on silica gel and subsequently kugelrohred under vacuum yielding the product as a clear, colorless oil (50 g, 0.041 moles), BP 40° C./11.4 mm.

Analysis: IR: 3348 (broad), 2969, 2934, 2874, 1462, 1454, 1446, 1413, 1377, 1344, 1309, 1299, 1210, 1172, 1128, 1094, 1079, 1060, 1051, 1022, 1013, 997, 980, 951, 862, 721, and 649 cm$^{-1}$.

EXAMPLE 15

(5-Chloro-3-pentyloxy)(2,2-dimethylethyl)dimethylsilane

The procedure followed is the same as that described in Example 19 substituting 5-chloropentan-3-ol (1-chloro-3-pentanol) (50 g, 0.41 moles), tert-butyldimethylsilyl chloride (71 g, 0.47 moles), imidazole (32.6 g, 0.48 moles), and dimethylformamide (150 ml). The crude product is fractionally distilled under vacuum leaving a clear, colorless oil (78 g, 0.33 moles), BP 48° C./0.1 mm.

Analysis: IR: 2958, 2933, 2892, 2887, 2859, 2826, 2803, 1472, 1463, 1447, 1468, 1389, 1374, 1361, 1337, 1310, 1293, 1280, 1257, 1212, 1185, 1175, 1168, 1135, 1088, 1043, 1032, 1006, 958, 939, 913, 901, 837, 809, 775, 730, 712, 676, and 654 cm$^{-1}$.

EXAMPLE 16

3-(3-[(1,1-Dimethylethyl)dimethylsiloxy]pent-1-yl)cyclopentene [3-(2-cyclopenten-1-yl)-1-ethylpropoxy](1,1-dimethylethyl) dimethylsilane The procedure followed is the same as that described in Example 20 substituting (5-chloro-3-pentyloxy)(2,2-dimethylethyl)dimethylsilane {3-chloro-1-ethylpropoxy)(1,1-dimethylethyl) dimethylsilane,} (78 g, 0.33 moles) diluted in tetrahydrofuran (100 ml), granular magnesium (24 g, 1.00 moles) in tetrahydrofuran (100 ml), 0.1 M solution of Li$_2$CuCl$_4$ (1.0 mmole), 3-chlorocyclopentene (33 g, 0.33 moles) diluted in tetrahydrofuran (50 ml). The crude product is distilled under reduced pressure leaving a clear yellow oil (21 g, 0.078 moles), BP 69° C./ 0.1 mm.

Analysis: IR: 3055, 2956, 2933, 2902, 2858, 1472, 1463, 1374, 1361, 1256, 1136, 1097, 1060, 1035, 1006, 835, 806, 774, 717, and 661 cm$^{-1}$.

EXAMPLE 17A

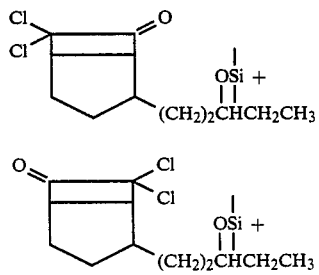

Alpha and beta isomers of 6,6-dichloro-2-(3-[1,1-dimethylethyl)dimethylsiloxy]-pent-1-yl)bicyclo[3.2.0]heptan-7-one {7,7-dichloro-4-[3,[[(1,1-dimethylethyl)dimethylsilyl]oxy]pentyl]bicyclo[3.2.0]heptan-6-one} and 7,7-dichloro-2-(3-[(1,1-dimethylethyl)dimethylsiloxyl]pent-1-yl)bicyclo[3.2.0]heptan-6-one {7,7-dichloro-2-[3,[[(1,1-dimethylethyl)dimethylsilyl]oxy]pentyl]bicyclo[3.2.0]heptan-6-one}

The procedure followed is the same as that described in Example 21A substituting 3-(3-[(1,1-dimethylethyl)-dimethylsiloxy]pent-1-yl)cyclopentene {[3-(2-cyclopenten-1-yl)-1-ethylpropoxy](1,1-dimethylethyl)dimethylsilane} (15 g, 0.056 moles) diluted in ether (100 ml), trichloroacetyl chloride (20.3 g, 0.11 moles) and phosphorous oxychloride (17.2 g, 0.11 moles) both diluted with ether (50 ml), zinc/copper couple (10 g, 0.16 moles). The crude product is kugelrohred under vacuum leaving a clear yellow oil (13.5 g, 0.035 moles).

Analysis: IR: 2953, 2932, 2903, 2858, 1806, 1471, 1463, 449, 1374, 1361, 1256, 1184, 1135, 1099, 1065, 1052, 1031, 1006, 966, 960, 939, 898, 835, 808, 774, 740, and 674 cm$^{-1}$.

EXAMPLE 17B

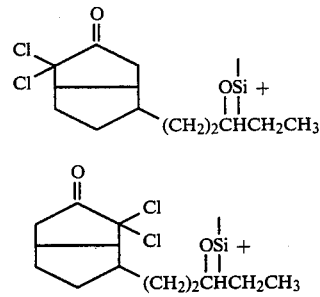

Alpha and beta isomers of 6,6-dichloro-2-(3-[(1,1-dimethyl-ethyl) siloxy]pent-1-yl)bicyclo[3.3.0]octan-7-one and 8,8-dichloro-2-(3-[(1,1-dimethylethyl)dimethylsiloxy]-pent-1-yl)bicyclo[3.3.0]octan-7-one {1,1-dichloro6-[3-[[(1,1-dimethylethyl)dimethylsilyl]oxy]pentyl]hexahydro2(1H)-pentalenone Diazomethane is generated in situ from N-methyl-N-nitroso- p-toluenesulfonamide (60 g, 0.28 moles) according to the standard procedure using the macro diazald kit (Aldrich). The starting material used in the previous example, 6,6-dichloro-2-(3-[(1,1dimethylethyl)dimethylsiloxy]pent-1-yl)bicyclo[3.2.0]heptan-7one and isomers (8.5 g, 0.023 moles), is treated with ether diazomethane solution (100 ml) followed by methanol (4 ml). After 50 minutes the excess diazomethane is neutralized with the addition of acetic acid (10 ml). The solution is extracted with ether and the solution is neutralized with a solution of saturated bicarbonate and then dried over anhydrous sodium sulfate. The solvent is removed under vacuum leaving a clear yellow oil. The crude product is chromatographed on silica gel leaving a clear light yellow oil (3.3 g, 8.5 mmoles).

Analysis: IR: 2957, 2933, 2884, 2859, 1769, 1472, 1463, 1450, 1389, 1375, 1361, 1281, 1273, 1256, 1186, 1136, 1097, 1080, 1051, 1005, 961, 939, 929, 891, 836, 808, 774, 744, 711, 675, and 661 cm$^{-1}$.

EXAMPLE 18

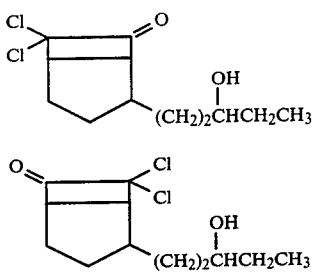

Alpha and beta isomers of
6,6-dichloro-2-(3-hydroxypent-1-yl)bicyclo[3.2.0]heptan-7-one
{7,7-dichloro-4-(3-hydroxypentyl)bicyclo[3.2.0]heptan-6-one} and 7,7-dichloro-2-(3-hydroxypent-1-yl) bicyclo[3.2.0]heptan-6-one
{7,7-dichloro-2-(3-hydroxypentyl)bicyclo[3.2.0]heptan-6-one}

The product from Example 17A, 6,6-dichloro-2-(3[(1,1dimethylethyl)dimethylsiloxy]pent-1-yl)bicyclo[3.2.0]heptan-7one {7,7-dichloro-4-[3,[[(1,1-dimethylethyl)dimethylsilyl]oxy]pentyl]bicyclo[3.2.0]heptan-6-one} and isomers (0.9 g, 2.4 mmoles) is diluted with acetonitrile (20 ml) and a 40% stock solution of hydrofluoric acid (1 ml) is added. The reaction is stirred at room temperature for 10 minutes and then slowly neutralized with a saturated solution of sodium bicarbonate. The reaction is partitioned between ether (1500 ml) and the aqueous phase extracted with ether (1×1000 ml). The organic extracts are combined and the solvent volume reduced under vacuum. The residue is dried over anhydrous sodium sulfate and the remaining solvent removed leaving a clear, colorless oil. The product is kugelrohred under vacuum leaving a product sufficiently pure for the next reaction (0.55 g, 2.0 moles).

Analysis: IR: 3411 (broad), 2964, 2940, 2870, 1803, 1462, 1450, 1376, 1334, 1301, 1287, 1225, 1159, 1125, 1106, 1097, 1062, 1030, 1006, 1002, 964, 948, 938, 914, 871, 830, 818, 790, 743, and 675 cm$^{-1}$.

EXAMPLE 19

(5-Chloro-1-pentyloxy)(2,2-dimethylethyl)dimethylsilane
{(5chloropentyl)oxy](1,1-dimethylethyl)dimethylsilane}

5-Chloropentanol (325 g, 2.65 moles) is added to a solution containing tert-butyldimethylsilyl chloride (439 g, 2.91 moles) and dimethylformamide (1.625 liters). Imidazole (199 g, 2.91 moles) is added in one portion and the solution is stirred at room temperature for 6 hours, after which time water (1 liter) is added and the reaction partitioned with hexanes. The organic phase is separated and the solvent volume reduced under vacuum. The residue is dried over anhydrous magnesium sulfate and the remaining solvent removed under vacuum leaving a clear, colorless oil. The crude product is subsequently fractionally distilled under reduced pressure leaving the product as a clear, colorless oil (534 g, 2.26 moles), BP 71° C./0.3 mm.

Analysis: IR: 2958, 2930, 2898, 2862, 2802, 2739, 1472, 1463, 1447, 1434, 1407, 1389, 1361, 1353, 1291, 1257, 1218, 1153, 1106, 1055, 1031, 1024, 1007, 983, 939, 928, 913, 836, 813, 776, 727, 678, and 657 cm$^{-1}$.

EXAMPLE 20

3-(5-[(1,1,Dimethylethyl)dimethylsiloxy]pent-1-yl)cyclopentene

All reactions are carried out under nitrogen atmosphere. The starting material, (5-chloro-1-pentyloxy)(2,2-dimethylethyl) dimethylsilane {[(5-chloropentyl)oxy](1,1-dimethylethyl)dimethylsilane} (534 g, 2.26 moles), is diluted in tetrahydrofuran (500 ml) and added in portions to a refluxing solution of tetrahydrofuran containing granular magnesium (75 g). After the addition is complete the reaction is refluxed an additional 2 hours, the Grignard salt is cooled to room temperature and cannulated into a three liter flask. The reaction vessel is cooled to −20° C. and and stirred while a solution of Li$_2$CuCl$_4$ (6.4 mmoles) is added followed by the dropwise addition of 3-chlorocyclopentene (219 g, 2.1 moles) chilled in a −30° C. dry ice/ethanol bath. After the addition is complete the reaction is warmed to room temperature. Water (500 ml) is added and the reaction partitioned with hexane. The lower phase is extracted with hexane (3×400 ml) and combined with the upper phase. The volume is reduced and the residue washed with brine (2×500 ml). The organic layer is dried over anhydrous sodium sulfate and the remaining solvent removed under vacuum leaving a clear yellow oil. The crude product is fractionally distilled under reduced pressure leaving a clear, colorless oil (478 g, 1.78 moles) BP 96° C./0.3 mm.

Analysis: IR: 3049, 2948, 2928, 2854, 1469, 1460, 1387, 1359, 1254, 1103, 1052, 1027, 1005, 938, 834, 811, 773, 715, 676, and 661 cm$^{-1}$.

EXAMPLE 21A

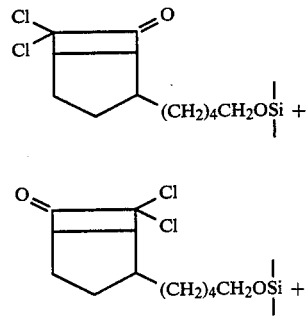

Alpha and beta isomers of
6,6-dichloro-2-(5-[(1,1,-dimethylethyl)-dimethylsiloxy]-pent-1-ylbicyclo[3.2.0]heptan-7-one {7,7-dichloro-4-[5-[[(1,1-dimethylethyl)dimethylsilyl]oxy]pentyl]bicyclo[3.2.0]heptan-6-one} and
7,7-dichloro-2-(5-[(1,1,-dimethylethyl)dimethylsiloxy]-pent-lyl)bicyclo[3.2.0]heptan-6-one
{7,7-dichloro-2-[5-[[(1,1-dimethylethyl)dimethylsilyl]oxy]pentyl]bicyclo[3.2.0]heptan-6-one}

A solution containing trichloroacetyl chloride (149 g, 0.82) and phosphorous oxychloride (126 g, 0.82 mole) diluted with ether (600 ml) is added dropwise to the reaction vessel containing zinc/copper couple (54 g, 0.82 moles) and the starting material, 3-(5-[(1,1-dimethylethyl)dimethylsiloxy]pent-1-yl)cyclopentene (200 g, 0.745 moles) diluted in ether (2 liter). After the addition is complete the reaction is refluxed for 4 hours. The vessel is cooled to room temperature and the reaction neutralized by the slow addition of a saturated solution of sodium bicarbonate. The solution is filtered, the phases separated, and the aqueous layer is extracted with ether (2×1000 ml). The extracts are combined and dried over sodium sulfate, and the solvent is removed under vacuum leaving the clear yellow oil. The crude product is kugelrohred and then fractionally distilled under vacuum leaving the product as a clear, colorless oil (148 g, 0.392 moles), BP 178° C./0.25 mm.

Analysis: IR: 2950, 2929, 2897, 2855, 1804, 1460, 1447, 1405, 1386, 1359, 1301, 1271, 1254, 1223, 1185, 1157, 1100, 1057, 1029, 1005, 974, 962, 937, 923, 901, 835, 813, 774, 741 and 673 cm$^{-1}$.

EXAMPLE 21B

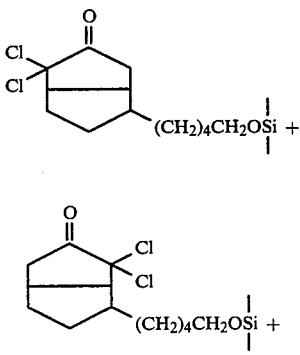

Alpha and beta isomers of
6,6-dichloro-2-(5-[(1,1-dimethylethyl)dimethylsiloxy]pent-1-ylbicyclo[3.3.0]octan-7-one
{1,1-dichloro4-[5-[[(1,1-dimethylethyl)dimethylsilyl]oxy]pentyl]hexahydro2(1H)-pentalenone} and
7,7-dichloro-2-(5-[1,1-dimethylethyl)dimethylsiloxy](-pent-1-yl)bicyclo[3.3.0]octan-6-one
{1,1-dichloro6-[5-[[(1,1-dimethylethyl)dimethylsilyl]oxy]pentyl]hexahydro2(1H)-pentalenone Diazomethane is generated in situ from N-methyl-N-nitroso-p-toluenesulfonamide (60 g, 0.28 moles) according to the standard procedure using the macro diazald kit (Aldrich). The product of the preceding example, containing mainly 6,6-dichloro-2-(5[(1,1,-dimethylethyl)dimethylsiloxy]pent-1-yl)bicyclo[3.2.0]heptan-7-one {7,7-dichloro-4-[5-[[(1,1-dimethylethyl)dimethylsilyl]oxy]pentyl]bicyclo[3.2.0]heptan-6-one} (30 g) and isomer are diluted with ether (300 ml) is treated with etheral diazomethane and methanol (4 ml). After 50 minutes, the excess diazomethane is neutralized by the slow addition of glacial acetic acid (15 ml). The reaction is neutralized with a solution of saturated sodium bicarbonate and then dried over anhydrous sodium sulfate. The solvent is removed under vacuum leaving a clear, yellow oil. The crude product is chromatographed on silica gel leaving a clear, colorless oil (12.1 g, 0.30 moles).

Analysis: IR: 2949, 2928, 2853, 1768, 1468, 1460, 1403, 1386, 1358, 1254, 1187, 1099, 1005, 979, 937, 919, 890, 834, 810, 774, 710, 658, and 633 cm$^{-1}$.

EXAMPLE 22A

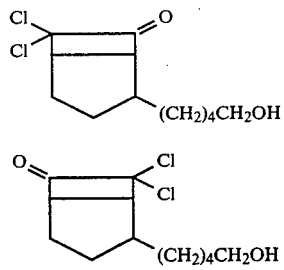

Alpha and beta isomers of
6,6-dichloro-2-(5-hydroxypent-1-yl)
bicyclo[3.2.0]heptan-7-one
{7,7-dichloro-4-(5-hydroxypentyl)bicyclo[3.2.0]heptan-6-one} and 7,7-dichloro-2-(5-hydroxypent-1-yl)
bicyclo[3.2.0]heptan-6-one
{7,7-dichloro-2-(5-hydroxypentyl)bicyclo[3.2.0]heptan-6-one}

The procedure followed is the same as that described in Example 18 substituting the product of Example 21A, containing 6,6-dichloro-2-(5-[(1,1-dimethylethyl)dimethylsiloxy]pent-1-yl) bicyclo[3.2.0]heptan-7-one {7,7-dichloro-4-[5-[[(1,1-dimethylethyl)dimethylsilyl]oxy]-pentyl]bicyclo[3.2.0]heptan-6-one} and isomers (32.1 g, 0.084 moles), hydrofluoric acid (8.0 ml), and acetonitrile (161 ml). The crude product is chromatographed on silica gel and subsequently kugelrohred under vacuum leaving a clear, colorless oil (20.1 g, 0.076 moles).

Analysis: IR: 3406 (broad), 2931, 2856, 1801, 1460, 1372, 1348, 1334, 1318, 1302, 1276, 1223, 1159, 1131, 1073, 1055, 1028, 992, 987, 970, 959, 915, 817, 739, and 623 cm$^{-1}$.

EXAMPLE 22B

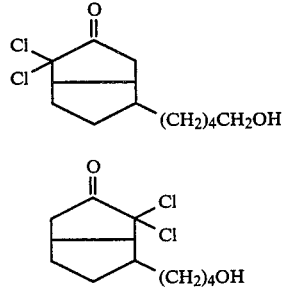

Alpha and beta isomers of
6,6-dichloro-2-(5-hydroxypent-1-yl)bicyclo[3.3.0]octan-7-one {1,1-dichlorohexahydro-4-(5-hydroxypentyl)-2(1H)-pentalenone} and
8,8-dichloro-2-(5-hydroxy-pent-1yl)bicyclo[3.3.0]octan-7-one {1,1-dichlorohexahydro-6-(5-hydroxypentyl)-2(1H)-pentalenone}

The procedure followed is the same as described in the previous Example substituting the product of Example 21B containing 6,6-dichloro-2-(5[(1,1-dimethylethyl)dimethylsiloxy]pent-1-yl)bicyclo[3.3.0]octan-7-one i1,1-dichloro-4-[5-[[(1,1-dimethylethyl)dimethylsilyl]oxy]pentyl]hexahydro-2(1H)-pentalenone) and isomer (2.0 g, 5.1 mmoles), acetonitrile (20 ml), and hydrofluoric acid (1.0 ml). The crude product is chromatographed on silica gel leaving a clear light yellow oil (1.2 g, 4.2 mmoles).

Analysis: IR: 3337 (broad), 2932, 2856, 1764, 1460, 1406, 1381, 1321, 891, 835, 818, 780, 763, 676, and 663 cm$^{-1}$.

EXAMPLE 23 3-(5-Hydroxypent-1-yl)cyclopentene {2-cyclopentene-1-pentanol}

3-(5-[(1,1,Dimethylethyl)dimethylsiloxy]pent-1-yl) cyclopentene (300 g, 1.70 moles) is diluted with acetonitrile (3000 ml) and a 40% stock solution of hydrofluoric acid (166 ml). The reaction is stirred at room temperature for 10 minutes and then slowly neutralized with a saturated solution of sodium bicarbonate. The reaction is partitioned between ether (1500 ml) and the aqueous phase extracted with ether (1×1000 ml). The organic extracts are combined and the solvent volume is reduced under vacuum. The residue is dried over anhydrous sodium sulfate and the remaining solvent removed leaving a clear, colorless oil. The product is kugelrohred under vacuum leaving a product sufficiently pure for the next reaction (171 g, 1.11 moles).

Analysis: IR: 3382 (broad), 3052, 2934, 2856, 1462, 1440, 1373, 1057, 1016, 717, 673, and 663 cm$^{-1}$. 3-(5-Cyclopenten-3-yl)valeraldehyde 2-cyclopentene-1-pentanal}

To 3-(5-hydroxypent-1-yl)cyclopentene {2-cyclopentene-1pentanol} (170 g, 1.10 moles) dissolved in methylene chloride (1552 ml) is added pyridinium dichromate (621 g, 1.65 moles). The solution is stirred at room temperature for 12 hours after which time isopropanol is added and the reaction stirred for 1 hour. The reaction is filtered through a pad of activated magnesium silicate (Florisil) and the solid rinsed with several portions of methylene chloride (3×400 ml). The solvent is removed under vacuum leaving a clear yellow oil. The crude product is kugelrohred under vacuum leaving a clear, colorless oil a (63 g, 0.414 moles).

Analysis: IR: 3052, 2934, 2854, 2719, 1731, 1462, 1442, 1411, 1392, 1361, 1285, 1260, 1178, 1166, 1150, 1091, 1055, 1034, 1007, 912, 719, and 612 cm$^{-1}$.

EXAMPLE 24 3-(5-Hydroxyhept-1-yl)cyclopentene {2-cyclopenten-1-pentanol}

All work is performed an inert atmosphere using anhydrous tetrahydrofuran. The starting material, 3-(5-cyclopenten-3-yl) valeraldehyde {2-cyclopentene-1-pentanal} (75 g, 0.493 moles) is diluted in tetrahydrofurar (750 ml) and cooled in a −30° C. ethanol/dry ice bath. Ethyl magnesium bromide (0.493 moles) is added dropwise to the stirring reaction mixture for a period of over 2 hours. The mixture is warmed to 0° C. and water (100 ml), followed by 15% sulfuric acid (200 ml), is added and the organic phase separated. The aqueous layer is extracted with ether (2×300 ml) and the organic extracts are combined. The volume is reduced and the residue washed with brine (400 ml). The product is dried over anhydrous sodium sulfate and the remaining solvent removed under vacuum leaving a clear yellow oil. The crude product is chromatographed on silica gel and subsequently kugelrohred under vacuum leaving clear, colorless oil (10.2 g, 0.056 moles).

Analysis: IR: 3387 (broad), 3054, 2930, 2875, 2857, 1463, 1441, 1432, 1422, 1413, 1378, 1360, 1331, 1314, 1284, 1262, 1250, 1147, 1118, 1064, 1054, 1037, 1025, 989, 970, 913, 717, 678 and 658 cm$^{-1}$.

EXAMPLE 25
3-(5-[(1,1-dimethylethyl)dimethylsiloxy]hept-1-yl)cyclopentene
{(5-[(2-cyclopenten-1-yl)-1-ethylpentyl]oxy]1,1-dimethylethyl) dimethylsilane}

The procedure followed is the same as that described in Example 19 substituting: 3-(5-hydroxyhept-1-yl)cyclopentene (32.5 g, 0.177 moles), t-butyldimethylsilyl chloride (29.3 g, 0.194 moles), imidazole (13.3 g, 0.194 moles), and dimethylformamide (163 ml). The crude product is fractionally distilled under reduced pressure leaving a clear, colorless oil (48 g, 0.162 moles), BP 103° C./0.15 mm.

Analysis: IR: 3046, 2925, 2850, 1460, 1445, 1404, 1374, 1358, 1252, 1214, 1183, 1127, 1108, 1064, 1055, 1005, 936, 909, 893, 857, 833, 812, 789, 771, 714, and 658 cm$^{-1}$.

EXAMPLE 26A

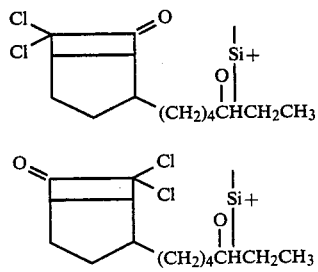

Alpha and beta isomers of
6,6-dichloro-2-(5-[(1,1-dimethylethyl) dimethylsiloxy]hept-1-yl)bicyclo[3.2.0]heptan-7-one
{7,7-dichloro-4-[5-[[(1,1-dimethylethyl)dimethylsilyl]oxy]bicyclo[3.2.0]heptan-6-one} and
7,7-dichloro-2-(5-[(1,1-dimethylethyl)dimethylsiloxy]-hept-1-yl)bicyclo[3.2.0]heptan-6-one
{7,7-dichloro-2-[5[[(1,1-dimethylethyl)dimethylsilyl]oxy]bicyclo[3.2.0]heptan-6-one}

The procedure followed is the same as that described in Example 21A substituting: 3-(5-[(1,1-dimethylethyl)-dimethylsiloxy]hept-1-yl)cyclopentene {([[5-(2-cyclopenten-1-yl)-1-ethylpentyl]oxy]1,1-dimethylethyl)dimethylsilane} (0.162 moles, 48.0 g), (23.3 g, 0.324 moles) of zinc copper couple, trichloroacetyl chloride (0.324 moles, 59 g, 36.2 ml) phosphorous oxychloride (0.324 moles, 50 g, 30.2 ml). The crude product is kugelrohred and fractionally distilled under reduced pressure leaving a clear, colorless oil (36 g, 0.088 moles), BP 168° C./0.3 mm.

Analysis: IR: 2827, 2876, 2852, 1802, 1460, 1405, 1376, 1359, 1306, 1252, 1223, 1182, 1158, 1129, 1109, 1066, 1029, 1012, 966, 936, 896, 859, 833, 789, 771, 740, 672, 622, and 619 cm$^{-1}$.

EXAMPLE 26B

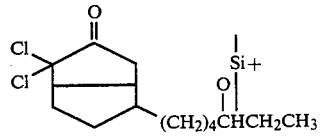

-continued

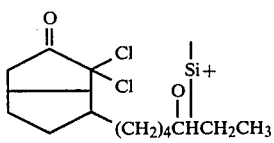

Alpha and beta isomers of
6,6-dichloro-2-(5-[(1,1-dimethylethyl)dimethylsiloxy]-hept-1-yl)bicyclo[3.3.0]octan-7-one
{1,1-dichloro4-[5-[[(1,1-dimethylethyl)dimethylsilyl 9 oxy]heptyl]hexahydro2(1H)-pentalenone} and
8,8-dichloro-2-(5-[(1,1-dimethYlethyl)dimethylsiloxyhept-1-yl)bicyclo[3.3.0]octan-7-one
{6-[5-(tertbutyldimethylsiloxy)heptyl]- b 1,1-dichlorohexahydro-2(1H)-pentalenone}

The procedure followed is the same as that described in Example 21B substituting: 6,6-dichloro-2-(5-[1,1-dimethylethyl) dimethylsiloxy]hept-1-yl)bicyclo[3.2.0-]heptan-7-one {7,7- dichloro-4-[5-[[(1,1-dimethylethyl)-dimethylsilyl]oxy]bicyclo [3.2.0]heptan-6-one]} and isomers (31.3 g, 0.093 moles) obtained in Example 26A. The crude product is chromatographed on silica gel leaving a clear yellow oil (9.7 g, 0.027 moles).

EXAMPLE 27

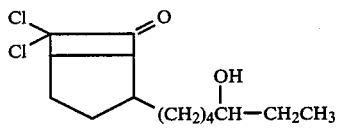

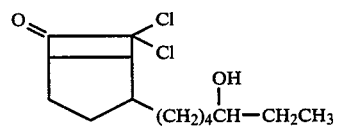

Alpha and beta isomers of
6,6-dichloro-2-(5-hydroxyhept-1-yl)bicyclo[3.2.0]heptan-7-one {7,7-dichloro-4-(5-hvdroxyheptyl) bicyclo[3.2.0]heptan-6-one} and
7,7-dichloro-2-(5-hydroxyhept-1yl)bicyclo[3.2.0]heptan-6-one {7,7-dichloro-2-(5-hydroxyheptyl) bicyclo[3.2.0]heptan-6-one}

The procedure followed is the same as that described in Example 18 substituting: 6,6-dichloro-2-(5-[(1,1-dimethylethyl) dimethylsiloxy]hept-1-yl)bicyclo[3.2.0-]heptan-7-one {7,7-di- chloro-4-[3,[[(1,1-dimethylethyl)-dimethylsilyl]oxy]pentyl]bicyclo [3.2.0]heptan-6-one} and isomers (21.8 g, 0.053 moles) of examples 26A, acetonitrile (436 ml), and 40% hydrofluoric acid (22 ml). The crude product is stirred chromatographed on silica gel and subsequently kugelrohred under vacuum leaving a clear, colorless oil (12.5 g, 0.475 moles).

Analysis: IR: 3408 (broad), 2959, 2935, 2874, 2860, 1804, 1463, 1455, 1445, 1376, 1319, 1304, 1281, 1250, 1247, 1225, 1159, 1135, 1116, 1090, 1065, 1031, 966, 924, 865, 855, 844, 811, 780, 742, 675 and cm$^{-1}$.

EXAMPLE 28

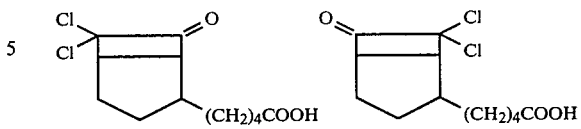

Alpha and Beta isomers of
6,6-dichloro-2-(5-carboxybut-1-yl) bicyclo[3.2.0]heptan-7-one
{6,6-dichloro-7-oxobicyclo[3.2.0]heptane-2-pentanoic acid} and 7,7-dichloro-2-(5-carboxybut-1-yl) bicyclo[3.2.0]heptan-6-one
{7,7-dichloro-6-oxobicyclo[3.2.0]heptane-2-pentanoic acid}

The product of Example 22A, containing 6,6-dichloro-2-(5-hydroxypent-1-yl)bicyclo[3.2.0]heptan-7-one {7,7-dichloro-4-(5-hydroxypentyl)bicyclo[3.2.0-]heptan-6-one} and isomer, (2.5 g, 9.5 mmoles) is mixed with a 10% solution of sodium carbonate (0.51 ml). The reaction is cooled in an ice bath and a solution of potassium permanganate (1.9 g, 2.2 mmoles, dissolved in 12 ml water) is slowly added over 10 minutes. The ice bath is then removed and the reaction stirred at room temperature for 12 hours, after which time the precipitated manganese dioxide is filtered off and the filtrate partitioned between ether. The solution is acidified with dilute sulfuric acid and the organic layer separated. The aqueous phase is extracted with ether (2×20 ml) and the extracts are combined and dried over anhydrous sodium sulfate and the solvent is removed under vacuum leaving a clear colorless oil. The crude product is chromatographed on silica gel and subsequently kugelrohred under reduced pressure leaving a clear, colorless oil (1.2 g, 4.3 mmoles).

Analysis: IR: 2930, 2854, 1803, 1460, 1375, 1348, 1338, 1315, 1302, 1160, 1131, 1073, 1055, 1028, 990, 950, 810, and 745 cm$^{-1}$.

EXAMPLE 29

(4-Chloro-1-butyloxy)(2,2-dimethylethyl)dimethylsilane
{(4chlorobutoxy)(1,1-dimethylethyl)dimethylsilane}

The procedure followed is the same as that described in Example 19 substituting 4-chlorobutanol (326 g, 3.00 moles), tert-butyldimethylsilyl chloride (500 g, 3.31 moles), imidazole (225 g, 3.30 mmoles), and dimethylformamide (1600 ml). The crude product is fractionally distilled under reduced vacuum leaving a clear, colorless oil (476 g, 2.13 moles), BP 60° C./0.3 mm.

Analysis: IR: 2952, 2928, 2889, 2855, 1469, 1462, 1443, 1387, 1359, 1277, 1255, 1106, 1005, 967, 835, 809, 774, 730, and 652 cm$^{-1}$.

EXAMPLE 30

3-(5-[(1,1-Dimethylethyl)dimethylsiloxy]but-1-y {[4(2-cyclopenten-1-yl)butoxy](1,1-dimethylethyl)-dimethylsilane}

The procedure followed is the same as that described in Example 20 with the following substituting (4-chloro-1-butyloxy) (2,2-dimethylethyl)dimethylsilane {(4-chlorobutoxy)(1,1-dimethylethyl)dimethylsilane} (476 g, 2.13 moles), tetrahydrofuran (500 ml), magnesium (96 g, 4.0 moles), 3-chlorocyclopentene (208 g, 2.0 moles), and Li$_2$CuCl$_4$ (6.4 mmoles). The resulting crude product is fractionally distilled under reduced pressure leaving a clear, colorless oil (100 g, 0.39 moles), BP 70° C./0.1 mm.

Analysis: IR: 3049, 2951, 2931, 2855, 1469, 1460, 1254, 1104, 1005, 834, 809, 773, 715 and 656 cm$^{-1}$.

EXAMPLE 31

3-(4-Hydroxybut-1-yl)cyclopentene {2-cyclopentene-1-butanol}

The procedure followed is the same as that described in Example 23 substituting 3-(5-[(1,1-dimethylethyl)-dimethylsiloxyl]but-1-yl)cyclopentene {[4-(2-cyclopenten-1-yl)butoxy](1,1-dimethylethyl)dimethylsilane} (100 g, 0.407 moles), 5% hydrofluoric acid (78 ml), and acetonitrile (1500 ml). The crude product is kugelrohred under reduced pressure leaving a clear, colorless oil (51 g, 0.36 moles).

Analysis: IR: 3340 (broad), 3332, 3048, 2930, 2851, 1457, 1439, 1371, 1358, 1282, 1249, 1072, 1056, 1034, 983, 937, 910, and 715 cm$^{-1}$.

EXAMPLE 32

3-(4-chlorobutyl)cyclopentene 3-(4-Hydroxybut-1-yl)cyclopentene {2-cyclopentene-1-butanol} (51 g, 0.37 moles) is diluted in dimethylformamide (100 ml) and added to pyridine (38 g, 0.40 moles). The solution is stirred and methanesulfonyl chloride (46 g, 0.40 moles) is added dropwise over 10 minutes. The reaction is partitioned between hexane (500 ml) and the organic phase separated. The aqueous layer is extracted with hexane (2×500 ml) and the organic extracts combined. The solvent volume is reduced under vacuum and the residue dried over anhydrous magnesium sulfate. The solid is filtered off and the remaining solvent removed leaving a clear yellow oil. The crude product is fractionally distilled under reduced pressure leaving a clear, colorless oil (43 g, 0.27 moles), BP 40°0/0.2 mm.

Analysis: IR: 3048, 2933, 2848, 1457, 1355, 1307, 1170, 910, 720 and 714 cm$^{-1}$.

EXAMPLE 33

3-(5-Hydroxyhept-1-yl)cyclopentene

All reactions are carried out under an inert atmosphere. 3-(4-Chlorobut-1-yl)cyclopentene {3-(4-chlorobutyl)cyclopentene} (43 g, 0.27 moles) is diluted in tetrahydrofuran (50 ml) and added dropwise to a stirred, refluxing solution of tetrahydrofuran (200 ml) containing granular magnesium (30 g, 1.25 moles). After the addition is complete and the resulting Grignard salt has formed the reaction is refluxed an additional 2 hours. The reaction vessel is then cooled in a 0° C. ice bath and propionaldehyde (15.6 g, 0.27 moles) diluted in tetrahydrofuran (20 ml) is added dropwise over 30 minutes. Then water (500 ml) is added over a period of 30 minutes and the reaction warmed to room temperature. The reaction is partitioned between ether (500 ml) and water. The aqueous layer is extracted with ether (2×500 ml) and the organic extracts are combined. The product is washed with brine (500 ml) and the solvent volume reduced under vacuum. The residue is dried over anhydrous magnesium sulfate and the solid filtered out. The remaining solvent is removed leaving a clear yellow oil. The crude product is fractionally distilled under reduced pressure leaving the desired product as a clear, colorless oil (52 g, 0.29 moles), BP 76° C./0.25 mm.

Analysis: IR: 3387 (broad), 3048, 2925, 2249, 1459, 1440, 1374, 1368, 1357, 1117, 1062, 1034, 1028, 968, and 715 cm$^{-1}$.

Alternatively to prepare longer chain homologues, other aldehydes can be substituted which include butyraldehyde, pentanal, etc. to form the corresponding derivatives 3-(5-hydroxyoct-1-yl)cyclopentene and 3-(5-hydroxyhept-1-yl) cyclopentene respectively. In addition the branched chain derivatives are easily formed by reacting the Grignard salt formed in Example 24 with acetone, 2-butanone, and other ketones to form 3-(5-methyl-5-hydroxyhex-1-yl)cyclopentene and 3(5-methyl-5-hydroxyhept-1-yl)cyclopentene, respectively. These intermediates can then be alkylated as described in Example 1 and (e.g. with methyl or ethyl iodide) and then reacted as described in Examples 21A and 21B to form the corresponding [3.2.0]and [3.3.0]bicyclo derivatives.

In addition the intermediate prepared in Example 23, 3-(5-hydroxypent-1-y)cyclopentene {3-(5-hydroxypentyl)cyclopentene} can be reacted by the same procedure described in Example 33 to form 3-(5-chloropent-1-yl)cyclopentene {3-(5-chloropentyl) cyclopentene} which can then be reacted as described in Example 26B to form the Grignard salt and thus can be used to form longer chain homologues in which the hydroxy group is in the 6 position. For example, reacting the Grignard salt with acetaldehyde would form 3-(6-hydroxyhept-1-yl)cyclopentene.

EXAMPLE 34

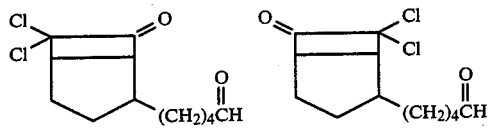

Alpha and beta isomers of
6,6-dichloro-2-(4-formylbutyl)[3.2.0]heptan-7-one
{6,6-dichloro-7-oxobicyclo[3.2.0]heptane-2-pentanol}
and 7,7-dichloro-2-(4-formylbutyl)[3.2.0]heptan-6-one
{7-di- chloro-6-oxobicyclo[3.2.0]heptane-2-pentanol}

The procedure followed is the same as that described in Example 8 substituting 6,6-dichloro-2-(5-hydroxy-pent-1-yl)bicyclo [3.2.0]heptan-7-one {7,7-dichloro-4-(5-hydroxypentyl)bicyclo [3.2.0]heptan-6-one, and isomers of Example 22A (2.3 g, 8.6 mmoles), and pyridinium dichromate (6.4 g, 17.1 mmoles) dissolved in methylene chloride (18 ml). The crude product is chromatographed on silica gel and subsequently kugelrohred under reduced pressure leaving a clear, colorless oil (0.9 g, 3.4 mmoles).

Analysis: IR: 2931, 2855, 2715, 1803, 1726, 1460, 1370, 1330, 1318, 1305, 1276, 1223, 1160, 1073, 1055, 1027, 992, 957, 950, 915, 817, 735 and 673 cm$^{-1}$.

EXAMPLE 35

3-Chlorocyclohexene

2-Cyclohexenol (30 g, 0.31 moles), is dissolved in a solution of dimethylformamide (100 ml) and pyridine (38 g, 0.40 moles). The solution is stirred and methanesulfonyl chloride (46 g, 0.40 moles) is added dropwise over 20 minutes. The reaction is then heated in a 70° C. water bath for 30 minutes, after which time the mixture is cooled and water (1 liter) is added over 20 minutes. The mixture is partitioned between hexane (500 ml) and the organic phase separated. The aqueous layer is extracted with hexane (2×500 ml) and the extracts are combined. The solvent volume is reduced under vacuum and the residue dried over anhydrous magnesium sulfate. The solid is filtered off and the remaining solvent removed leaving a clear yellow oil. The crude product is kugelrohred under reduced pressure leaving a clear, colorless oil (37 g, 0.28 moles).

EXAMPLE 36

3-(5-Methoxyhept-1-yl}cyclohexene
[3-(5-Methoxyheptyl)cyclohexene]

All work is performed under an inert atmosphere. The Grignard salt of the intermediate prepared in Example 37 is prepared using activated magnesium. The reaction vessel is charged with potassium metal (9.7 g, 0.248 moles), anhydrous magnesium chloride (24 g, 0.252 moles), and potassium iodide (41.8 g, 0.252 moles) and tetrahydrofuran (350 ml). The mixture is stirred, heated under reflux for 3 hours, and then cooled to room temperature. The starting material, 3-chlorocyclohexene (30 g, 0.224 moles) diluted in tetrahydrofuran (50 ml), is added and the reaction heated under reflux for 12 hours. Then the mixture is cooled in a −20° C. ice bath and Li$_2$CuCl$_4$ (0.6 mmoles) is added. The mixture is stirred for 10 minutes and 1-chloro-5-methoxyheptane (37 g, 0.224 moles), diluted in tetrahydrofuran, is added dropwise over 20 minutes. Then the mixture is poured into a saturated ammonium chloride solution and extracted with ether (500 ml) and water. The organic layer is separated and the aqueous layer extracted with ether (2×500 ml). The organic extracts are combined. The solvent is reduced under vacuum. The residue is washed with brine and then dried over anhydrous magnesium sulfate. The solid is filtered off and the remaining solvent removed leaving a clear, yellow oil. The crude product is chromatographed on silica gel and subsequently kugelrohred under reduced pressure leaving the product as a pale yellow oil (38 g, 0.13 moles).

Analysis: IR: 3055, 2925, 2900, 2865, 1469, 1378, 1355, 332, 1267, 1250, 1154, 1093 and 724 cm$^{-1}$.

EXAMPLE 37

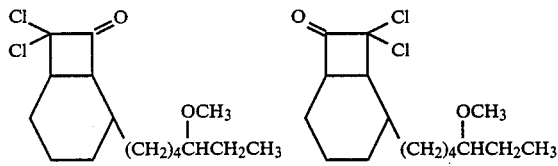

Alpha and Beta isomers of
7,7-dichloro-2-(5-methoxyhept-1-yl)bicyclo[4.2.0]octan-8-one {8,8-dichloro-5-(5-methoxyheptyl)bicyclo[4.2.0]octan-7-one} and
8,8-dichloro-2-(5-methoxyhept-1-yl)bicyclo[4.2.0]octan-7-one {8,8-dichloro-2-(5-methoxyheptyl)bicyclo[4.2.0]octan-7-one}

The procedure followed is the same as that described in Example 21A substituting 3-(5-methoxyhept-1-yl)cyclohexene {3-(5methoxyheptyl)cyclohexene} (38 g, 0.13 moles), trichloroacetyl chloride (43 g, 0.234 moles) and phosphorous oxychloride (39 g, 0.234 moles) both diluted in ether (100 ml), and zinc/copper couple (17 g, 0.26 moles). The crude product is chromatographed on silica gel and subsequently kugelrohred under reduced pressure leaving the product as a clear, colorless oil (21 g, 0.065 moles).

Analysis: IR: 2925, 2900, 2865, 1803, 1469, 1378, 1355, 1332, 1267, 1250, 1154, 1093, and 724 cm$^{-1}$.

EXAMPLE 38

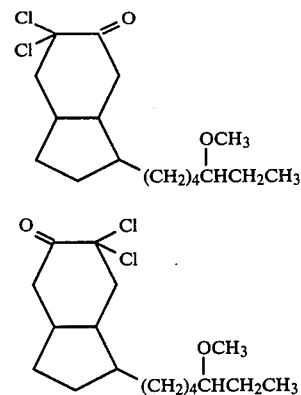

Alpha and Beta isomers of
7,7-dichloro-2-(5-methoxyhept-1-yl)bicyclo[4.3.0]nonan-8-one {6-dichlorooctahydro-3-(5-methoxyheptyl)-5H-inden-5-one} and
8,8-dichloro-2-(5-methoxyhept-1-yl) - bicyclo[4.3.0]nonan-8-one
{6-dichlorooctahydro-3-(5-methoxyheptyl)-5H-inden-5-one}

The procedure followed is the same as that described in Example 17B substituting 7,7-dichloro-2-(5-methoxyhept-1-yl) bicyclo[4.2.0]octan-8-one {8,8-dichloro-5-(5-methoxyheptyl)bicyclo[4.2.0]octan-7-one} and isomers (21 g, 0.065 moles) of the preceding Example, etheral diazomethane solution (282 ml), methanol (15 ml), and acetic acid (15 ml). After the acetic acid is added the solvent is removed under vacuum, leaving a clear yellow oil.

The crude product is then diluted with acetic acid (150 ml) and stirred while zinc powder (42 g) is slowly added. The reaction is heated in a 70° C. water bath for 1 hour, after which time ether (500 ml) is added and the solution is filtered. The filtrate is washed with brine (100 ml) and then with a solution of saturated bicarbonate. The ether layer is separated and dried over anhydrous sodium sulfate. The solvent is removed under vacuum leaving a clear yellow oil. The crude product is chromatographed on silica gel and subsequently kugelrohred under vacuum leaving a clear, colorless oil (5.1 g, 0.20 moles).

Analysis: IR: 2925, 2900, 2865, 1742, 1469, 1378, 1355, 1332, 1267, 1250, 1154, 1093, 960, and 745 cm$^{-1}$.

Salmon Assay

The compounds were tested against a variety of tumors in the Salmon assay [(Cancer Res. Report, Vol. 65, No. 1,(1981)]. Thus, in a typical test, 3 plates containing 40, 43 and 45 colonies of CHOW-5 (Chinese hamster ovary) cell line were incubated using a solution of 10 mcg of alpha 6,6-dichloro-2-(5-hydroxyhept-1-yl) bicyclo[3.2.0]heptan-7-one {7,7-dichloro-4-(5-hydroxyheptyl)bicyclo[3.2.0]heptan-6-one}. All treated colonies were destroyed. All controls survived.

In tests against Walker 256 rat carcinosarcoma, 10⁵ cells were implanted i.p. and the rats were treated i.p. daily on days 1-5. Alpha 6,6-dichloro-2-(5-methoxyhept-1-yl)bicyclo[3.2.0]heptan-7-one {7,7-dichloro-4-(5-methoxyheptyl)bicyclo[3.2.0]heptan-6-one} was dissolved in peanut oil. Untreated control rats lived an average of 8.0 days. Rats treated with 20% polyethylene glyco 400 in oil lived 8.5 days. Rats given 1 g/kg lived 12.5 days, significantly longer.

DEHALOGENATION

A. 6,6-dichloro-2-(5-methoxyhept-1-yl)bicyclo[3.3.0]octan-7-one {1,1-dichlorohexahydro-4-(5-methoxyheptyl)-2(1H)-pentalenone} or the isomer (45.9 g) are added to a single-neck 100 ml, round-bottom flask equipped with a condenser. The solution is stirred by a magnetic stirrer and powdered zinc metal (92 g) and glacial acetic acid (312 ml) are added and the solution heated under reflux for one hour, during which time white ZnCl₂ precipitates out of solution. The solution is filtered, washed with sodium hydrogen carbonate and extracted three times with ether. The ether extracts are combined and dried over anhydrous sodium sulfate. The resulting yellow oil is chromatographed with silica gel and eluted with 3:1 hexane:ether. The fractions are combined, yielding 2-(5-methoxyhept-1-yl)-bicyclo[3.3.0]octan7-one {hexahydro-4-(5-methoxyheptyl)-2(1H)-pentalenone} as a clear, colorless oil. B.

Analysis: IR: 2928, 2853, 2828, 1740, 1460, 1402, 1735, 1158, 1122, 1093, 1050, 1035, 960, and 740 cm⁻¹.

B. Zinc (3 g) is added to a stirred solution of 6,6-dichloro-2(5-methoxyhept-1-yl)bicyclo[3.2.0]heptan-7-one {7,7-dichloro-4(5-methoxyheptyl)bicyclo[3.2.0]heptan-6-one} (2 g, 6 moles) in acetic acid (100 ml) under a nitrogen atmosphere. The solution is stirred at room temperature for one hour, then refluxed for 13 hours, after which time the mixture is filtered through a sintered glass funnel and the ether solution dried over anhydrous sodium sulfate. The solvent is removed under vacuum, leaving the crude product. Chromatography on silica gel yields 2-(5-methoxyhept-1-yl)bicyclo[3.2.0]heptan-7-one {4-(5-methoxyheptyl) bicyclo[3.2.0]heptan-6-one} (1.2 g).

Analysis: IR: 2959, 2933, 2859, 2820, 1778, 1461, 1406, 1386, 1316, 1303, 1260, 1236, 1197, 1154, 1091, 1024, 921, 862, and 819 cm⁻¹.

C. Dehalogenation of 6,6-dichloro-2-(5-methoxyhept-1-yl)bicyclo[3.3.0]octan-7-ol {1,1-dichlorooctahydro-4-(5-methoxyheptyl)-2pentalenol} produces 2-(5-methoxyhept-1-yl)bicyclo[3.3.0]- octan-7-ol {octahydro-4-(5-methoxyheptyl)-2-pentalenol}.

Analysis: IR: 3501, 2960, 2932, 2856, 2822, 2736, 1657, 1638, 1635, 1461, 1374, 1303, 1261, 1248, 1246, 1239, 1161, 1132, 1093, 1037, 998, 963, 943, 920, 750, 724 and 690 cm⁻¹.

EXAMPLE 39

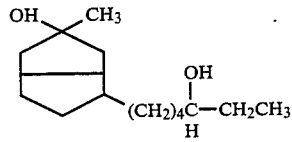

Alpha and beta isomers of 2-(5-methoxyhept-1-yl)-7-methyl-bicyclo [3.3.0]octan-7-ol {octahydro-4-(5-methoxyheptyl)-2-methyl-2-pentalenol}

6,6-Dichloro-2-(5-methoxyhept-1-6l)bicyclo[3.3.0]octan-7-one {1,1-dichlorohexahydro-4-(5-methoxyheptyl)-2(1H)-pentalenone} (4 g, 0.0158 moles) is added to a 400 ml ether solution of diazomethane, generated from 45 g of N-methyl-N-nitroso p-toluenesulfonamide. The reaction is allowed to proceed for 5 hours after which glacial acetic acid is added dropwise to neutralize the excess diazomethane. The ether solution is washed with sodium bicarbonate and dried over anhydrous sodium sulfate. The solvent is removed under vacuum, leaving an orange oil. This oil is applied in hexane and ether to a silica gel chromatography column and elution with 4:1 hexane-ether yields the product as a clear liquid. Infrared maxima are observed at 3430, 2931, 2856, 1658, 1461, 1379, 1362, 1329, 1325, 1316, 1244, 1195, 1173, 1162, 1093, 1027, 984, 950, and 923 cm⁻¹. Substitution in this reaction of 6,6-dichloro-2-(5-hydroxyhept-1-yl)bicyclo[3.3.0]octan-7-one {1,1-dichlorohexahydro-4-(5-hydroxyheptyl)-2(1H)pentalenone} leads to the corresponding 6,6-dichloro-2-(5-hydroxyhept-1-yl)-7-methyl-bicyclo[3.3.0]octan-7-ol {4,4-dichloroalpha-ethyloctahydro-5-hydroxy-5-methyl-1-pentalenepentano}.

2-(5-Methoxyhept-1-yl)bicyclo[3.3.0]octan-7-one hexahydro-4-(5-methoxyheptyl)-2(1H)-pentalenone, (4 g, 0.0158 moles) diluted in ether is added dropwise to a stirring solution of ethyl magnesium bromide (0.0158 moles) dissolved with diethyl ether. The mixture is cooled in an ice bath during the addition. The ice bath is removed and the solution stirred for an additional hour. The reaction is quenched with water and a 15% sulfuric acid solution. The organic phase is separated and the solvent removed under vacuum. The aqueous layer is extracted (2×200 ml) and the extracts are combined with the organic layer and dried over anhydrous sodium sulfate. The solid is filtered off and the remaining solvent removed leaving a clear, pale yellow oil. The crude product is subsequently chromatographed on silica gel yielding desired product as a clear colorless oil (1.7 g, 6.3 mmoles).

Analysis: IR: 3424 (broad), 2933, 2855, 2820, 1461, 1370, 1309, 1299, 1262, 1197, 1148, 1095, 949 and 920 cm⁻¹. An equivalent amount of methyl magnesium bromide can be used to make the 7-methyl homolog.

EXAMPLE 40

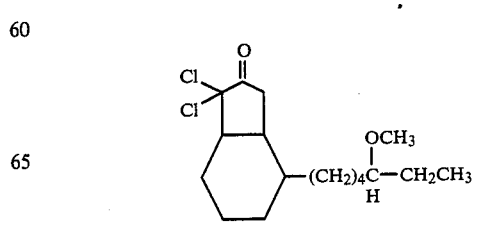

-continued

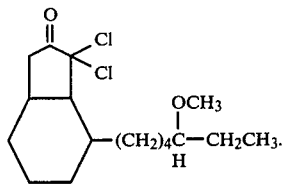

Alpha and Beta isomers of
7,7-dichloro-2-(5-methoxyhept-1-y1)bicyclo[4.3.0]nonan-8-one
{1,1-dichlorooctahydro-4-(5-methoxyheptyl)-2H-inden-2-one} and 9,9-dichloro-2-(5-methoxyhept-1-yl)bicyclc[4.3.0]nonan-8-one
{1,1-dichlorooctahydro-7-(5-methoxyheptyl)-2H-inden-2-one}

The procedure followed is the same as that described in Example 17A with the following substitutions made: the starting material from Example 37, 7,7-dichloro-2-(5-methoxyhept-1-yl) bicyclo[4.2.0]octan-8-one {8,8-dichloro-5-(5-methoxyheptyl)bicyclo[4.2.0]octan-7-one} and isomers (21 g, 0.065 moles), ether diazomethane solution (282 ml), methanol (15 ml), and acetic acid (15 ml). After the acetic acid is added the solvent is removed under vacuum, leaving a clear yellow oil.

The crude product is then diluted with acetic acid (150 ml) and stirred while zinc powder (42 g) is slowly added. The reaction is heated in a 70° C. water bath for 1 hour, after which time ether (500 ml) is added and the solution is filtered. The filtrate is washed with brine (100 ml) and then with a solution of saturated bicarbonate. The ether layer is separated and dried over anhydrous sodium sulfate. The solvent is removed under vacuum leaving a clear yellow oil. This oily product can be dehalogenated by the method of Example 4B to yield alpha and beta isomers of 2-(5-methoxyhept-1-yl)bicyclo[4.3.0]nonan-8-one {1,1-dichlorooctahydro-4-(5-methoxyheptyl)-2H-inden-2-one}. The crude product is chromatographed on silica gel and subsequently kugelrohred under vacuum leaving a clear, colorless oil (5.1 g, 0.20 moles).

Analysis: IR: 2925, 2900, 2865, 1742, 1469, 1378, 1355, 1332, 1267, 1250, 1154, 1093, 960, and 745 cm$^{-1}$.

What is claimed is:
1. A compound of the formula

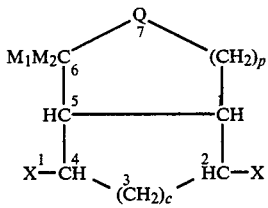

wherein
Q is CO or CH(OR),
R is hydrogen or methyl,
$M_1$ is halogen,
$M_2$ is halogen or hydrogen,
c is one or two
p is 0 or 1, and
one of X and X' is H and the other is hydroxy-$C^{2-9}$-alkyl, methoxy-$C^{2-9}$-alkyl, ethoxy-$C^{2-9}$-alkyl, oxo-$C^{2-9}$-alkyl, formyl-$C^{2-9}$-alkyl, carboxy-$C^{2-9}$-alkyl or ($C_{1-2}$-alkyl)oxycarbonyl-$C^{2-9}$-alkyl.

2. A compound of claim 1 wherein $M_1$ and $M_2$ are chlorine.

3. A compound of claim 2 wherein p is zero and c is one.

4. A compound of claim 3 wherein Q is CO and X' is H.

5. A compound of claim 4 which is 6,6-dichloro-2(5-hydroxyhept-1-yl)bicyclo[3.2.0]heptan-7-one.

6. A compound of claim 4 which is 6,6-dichloro-2-(5-methoxyhept-1-yl)bicyclo[3.2.0]heptan-7-one.

7. A compound of claim 4 wherein X is

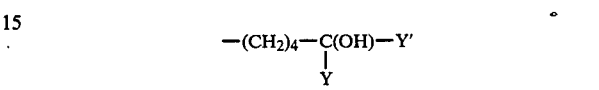

wherein Y and Y' are methyl or ethyl.,

8. A compound of claim 4 wherein X is oxo-$C^{2-9}$alkyl and X' is H.

9. A compound of claim 4 which is 6,6-dichloro-2-(5-oxohept-1-yl)bicyclo[3.2.0]heptan-7-one.

10. Compound of claim 2 wherein the group X is in the alpha position and X' is hydrogen.

11. Compound of claim 10 which is alpha-6,6-dichloro-2-(5-methoxyhept-1-yl)bicyclo[3.2.0]heptan-7-one.

12. A pharmaceutical composition for inhibition of tumors which contains an effective dose of a compound of the formula

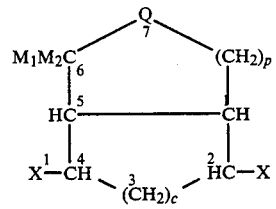

wherein
Q is CO or CH(OH),
$M_1$ is halogen,
$M_2$ is halogen or hydrogen,
c is one or two
p is 0 or 1, and
one of X and X' is H and the other is hydroxy-$C^{2-9}$-alkyl, methoxy-$C^{2-9}$-alkyl, ethoxy-$C^{2-9}$-alkyl, oxo-$C^{2-9}$-alkyl, formyl-$C^{2-9}$-alkyl, carboxy-$C^{2-9}$-alkyl or ($C_{1-2}$-alkyl)oxycarbonyl-$C^{2-9}$-alkyl. and a pharmaceutically acceptable carrier.

13. A composition of claim 12 wherein Mhd 1 and $M_2$ are chlorine.

14. A composition of claim 13 wherein p is zero.

15. A composition of claim 10 wherein X is oxoalkyl.

16. A composition of claim 15 wherein the compound is 6,6-dichloro-2-(5-oxohept-1-yl)bicyclo[3.2.0]heptan-7-one.

17. A composition of claim 14 wherein Q is CO.

18. A composition of claim 14 wherein the compound is 6,6-dichloro-2-(5-hydroxyhept-1-yl)bicyclo[3.2.0]heptan-7-one.

19. A composition of claim 14 wherein the compound is 6,6-dichloro-2-(5-methoxyhept-1-yl)bicyclo[3.2.0]heptan-7-one.

20. A composition of claim 14 wherein X is

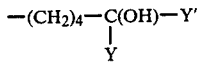

wherein Y and Y' are methyl or ethyl.

21. A method for inhibiting tumors in a mammal which comprises administration of an effective inhibitory dose of a compound of the formula

H

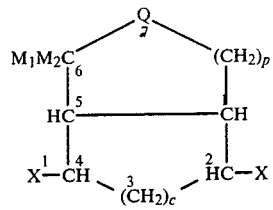

wherein
Q is CO or CH(OH),
$M_1$ is halogen,
$M_2$ is halogen or hydrogen,
c is one or two
p is 0 or 1 and one of X and X' is H and the other is hydroxy-$C^{2-9}$ alkyl, methoxy-$C^{2-9}$-alkyl, ethoxy-$C^{2-9}$-alkyl or oxo-$C^{2-9}$-alkyl, formyl-$C^{2-9}$-alkyl, carboxy-$C^{2-9}$-alkyl or ($C_{1-2}$-alkyl)oxycarbonyl-$C^{2-9}$-alkyl.

* * * * *